(12) United States Patent
Chen et al.

(10) Patent No.: US 10,166,140 B2
(45) Date of Patent: Jan. 1, 2019

(54) LIQUID CONTAINER AND ABSORBENT INSERT FOR ORAL NEGATIVE-PRESSURE THERAPY SYSTEM

(71) Applicant: Somnics, Inc., Zhubei (TW)

(72) Inventors: Chung Chu Chen, Zhubei (TW); Chen Ning Huang, Zhubei (TW); Tung Ming Yu, Zhubei (TW); Yin Ruei Chen, Zhubei (TW); Chih Jung Lee, Zhubei (TW); Chin Jen Lin, Zhubei (TW); Ming Tsung Kuo, Zhubei (TW)

(73) Assignee: SOMNICS, INC., Zhubei (TW)

( * ) Notice: Subject to any disclaimer, the term of this patent is extended or adjusted under 35 U.S.C. 154(b) by 497 days.

(21) Appl. No.: 14/867,657

(22) Filed: Sep. 28, 2015

(65) Prior Publication Data

US 2016/0375183 A1 Dec. 29, 2016

Related U.S. Application Data

(60) Provisional application No. 62/184,835, filed on Jun. 25, 2015.

(51) Int. Cl.
*A61F 5/56* (2006.01)
*A61M 1/00* (2006.01)
(Continued)

(52) U.S. Cl.
CPC .......... *A61F 5/566* (2013.01); *A61M 1/0001* (2013.01); *A61M 1/0094* (2014.02); *A61C 17/04* (2013.01);
(Continued)

(58) Field of Classification Search
CPC . A61F 5/56; A61F 5/566; A61C 17/04; A61C 17/043; A61C 17/046;
(Continued)

(56) References Cited

U.S. PATENT DOCUMENTS

| 2,937,445 A | 5/1960 | Erickson |
| 3,132,647 A | 5/1964 | Corniello |

(Continued)

FOREIGN PATENT DOCUMENTS

| CN | 102996530 A | 3/2013 |
| CN | 103263315 A | 8/2013 |

(Continued)

OTHER PUBLICATIONS

Colrain et al. "A Multi-Centre Evaluation of Oral Pressure Therapy for the Treatment of Obstructive Sleep Apnea." SRI International, ApniCure, Inc. Abstract/Pamphlet, 2012.

(Continued)

*Primary Examiner* — Keri J Nelson
(74) *Attorney, Agent, or Firm* — Stinson Leonard Street LLP

(57) ABSTRACT

An oral negative-pressure therapy system includes a container and absorbent insert for the container. The container includes a baffle inside an interior of the container. A fluid passageway extends along the baffle for delivering fluid (e.g., a mixture of air and saliva) into the container. The absorbent insert for absorbing liquid (e.g., saliva) in the container may is over the baffle. At least one of the baffle and the absorbent insert is configured to maintain a fluid flow path between the baffle and the absorbent insert to maintain fluid communication between a fluid inlet and a fluid outlet of the container. The absorbent insert and/or the container may be designed and constructed to burst air bubbles in the aspirated liquid. In one or more embodiments, the absorbent insert is replaceable so that a spent absorbent insert can be replaced with a new, fresh absorbent insert.

22 Claims, 20 Drawing Sheets

(51) Int. Cl.
*A61M 16/04* (2006.01)
*A61C 17/06* (2006.01)

(52) U.S. Cl.
CPC ......... *A61M 1/0023* (2013.01); *A61M 1/0058* (2013.01); *A61M 16/049* (2014.02); *A61M 16/0488* (2013.01); *A61M 2202/0466* (2013.01); *A61M 2210/0625* (2013.01)

(58) Field of Classification Search
CPC .............. A61M 1/0023; A61M 1/0058; A61M 16/0488; A61M 16/049
USPC .................... 128/848, 205.27; 433/91–96
See application file for complete search history.

(56) References Cited

U.S. PATENT DOCUMENTS

| | | | |
|---|---|---|---|
| 4,169,473 | A | 10/1979 | Samelson |
| 4,304,227 | A | 12/1981 | Samelson |
| 4,669,459 | A | 6/1987 | Spiewak et al. |
| 4,676,240 | A | 6/1987 | Gardy |
| 4,791,914 | A | 12/1988 | May |
| 5,050,616 | A | 9/1991 | Wolff et al. |
| 5,104,315 | A | 4/1992 | McKinley |
| 5,465,734 | A | 11/1995 | Alvarez et al. |
| 5,588,836 | A | 12/1996 | Landis et al. |
| 5,616,158 | A * | 4/1997 | Biendarra ............ B01D 53/261 128/205.27 |
| 5,692,523 | A | 12/1997 | Croll et al. |
| 5,876,199 | A | 3/1999 | Bergersen |
| 5,915,385 | A | 6/1999 | Hakimi |
| 5,957,133 | A | 9/1999 | Hart |
| 6,494,209 | B2 | 12/2002 | Kulick |
| 6,569,133 | B2 | 5/2003 | Cheng et al. |
| 6,679,257 | B1 | 1/2004 | Robertson et al. |
| 6,820,617 | B2 | 11/2004 | Robertson et al. |
| 6,877,513 | B2 | 4/2005 | Scarberry et al. |
| 6,955,172 | B2 | 10/2005 | Nelson et al. |
| 6,976,491 | B2 | 12/2005 | D'Agosto |
| 6,997,186 | B2 | 2/2006 | Robertson et al. |
| 7,073,505 | B2 | 7/2006 | Nelson et al. |
| 7,073,506 | B2 | 7/2006 | Robertson et al. |
| 7,182,082 | B2 | 2/2007 | Hoffrichter |
| 7,328,698 | B2 | 2/2008 | Scarberry et al. |
| 7,997,275 | B2 * | 8/2011 | Quinn .................... A01N 25/34 128/201.11 |
| 8,091,554 | B2 | 1/2012 | Jiang |
| 8,122,890 | B2 | 2/2012 | Vaska |
| 8,308,705 | B2 | 11/2012 | Lin et al. |
| 8,979,823 | B2 | 3/2015 | Podmore et al. |
| 2003/0208149 | A1 | 11/2003 | Coffey |
| 2005/0166928 | A1 | 8/2005 | Jiang |
| 2005/0166929 | A1 | 8/2005 | Jiang |
| 2005/0217678 | A1 | 10/2005 | McCormick et al. |
| 2005/0236003 | A1 | 10/2005 | Meader |
| 2006/0096600 | A1 | 5/2006 | Witt et al. |
| 2006/0282010 | A1 | 12/2006 | Martin et al. |
| 2007/0277818 | A1 | 12/2007 | Chen |
| 2008/0188947 | A1 | 8/2008 | Sanders |
| 2008/0210244 | A1 | 9/2008 | Keropian |
| 2008/0216843 | A1 | 9/2008 | Jiang |
| 2009/0120446 | A1 | 5/2009 | Vaska et al. |
| 2009/0288660 | A1 | 11/2009 | Chen et al. |
| 2010/0147302 | A1 | 6/2010 | Selvarajan et al. |
| 2011/0192404 | A1 | 8/2011 | Chen |
| 2011/0220124 | A1 | 9/2011 | Vaska et al. |
| 2012/0021375 | A1 | 1/2012 | Binner et al. |
| 2013/0226120 | A1 | 8/2013 | Van De Maele |
| 2014/0014112 | A1 | 1/2014 | Vitale et al. |
| 2014/0034064 | A1 | 2/2014 | Chen et al. |
| 2014/0360509 | A1 | 12/2014 | Podmore et al. |
| 2015/0107603 | A1 | 4/2015 | Podmore et al. |

FOREIGN PATENT DOCUMENTS

| | | |
|---|---|---|
| WO | 2012048879 A1 | 4/2012 |
| WO | 2013149078 A1 | 10/2013 |
| WO | 2014028993 A1 | 2/2014 |

OTHER PUBLICATIONS

Colrain et al. "A Multi-Centre Evaluation of Oral Pressure Therapy for the Treatment of Obstructive Sleep Apnea: Sleep architecture effects." SRI International, ApniCure, Inc., 2012.

Engelke et al. "Preliminary radiographic observations of the tongue-repositioning manoenvre." European Journal of Orthodontics, 28, 2006, pp. 618-623, Oxford University Press.

Engelke et al. "Functional Treatment of Snoring Using Oral Shields in Conjunction with the Tongue Respositioning Manoevre." Int. J. Odontostornat., 1(2) 2007, 133-139.

Engelke et al. "Functional Treatment of Snoring based on the tongue-repositioning manoenvre." European Journal of Orthodontics, 32, 2010, pp. 490-495, Oxford University Press.

Lazard et al. "The Tongue-Retaining Device: Efficacy and Side Effects in Apnea Syndrome." Journal of Clinical Sleep Medicine vol. 5, No. 5, 2009, pp. 431-438, France.

Malhotra et al. "Oral Pressure Therapy Improves Obstructive Sleep Apnea." Am J Respir Crit Care Med 2012, Abstract.

Schwab et al. "Examining the mechanism of action of a new device using oral pressure therapy of the treatment of obstructive sleep apnoea." Sleep Disordered breathing-treatment, 21st Congress of the European Sleep Research Society, Sep. 8, 2012, 1 page, Paris, France.

Schwab et al. "Mechanism of Action of a New Device Using Oral Pressure Therapy (OPT) for the treatment of OSA." Center for Sleep and Circadian Neurobiology, Univ. of Pennsylvania School of Medicine, Pamphlet, 2012.

* cited by examiner

LIQUID CONTAINER AND ABSORBENT INSERT FOR ORAL NEGATIVE-PRESSURE THERAPY SYSTEM

CROSS-REFERENCE TO RELATED APPLICATION

The present application claims the benefit of U.S. Provisional Application Ser. No. 62/184,835, filed Jun. 25, 2015, the entirety of which is hereby incorporated by reference.

FIELD OF THE DISCLOSURE

The present disclosure generally relates to an oral negative-pressure therapy system, a liquid container for the oral negative-pressure therapy system, and absorbent insert for the liquid container.

BACKGROUND OF THE DISCLOSURE

Obstructive sleep apnea (OSA), hypopnea, and upper airway resistance syndrome (UARS) are among a variety of known disorders characterized by episodes of complete or partial upper airway obstruction during such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and/or UARS experience repeated, frequent arousal from sleep in response to the oxygen deprivation. The arousals result in sleep fragmentation and poor sleep continuity.

To treat such disorders, it has been proposed to apply a negative pressure to a user's oral cavity. For example, an appliance for treating obstructive sleep apnea (OSA) may utilize a device held in a patient's mouth where a vacuum is constantly drawn on the device in order to reposition portions of the patient's oral anatomy to reduce the likelihood of OSA. For example, the vacuum may be drawn in order to help draw the soft palate and/or rear portion of a patient's tongue away from the pharynx in order to maintain a clear breathing passage. In such devices which draw a partial negative pressure within the oral cavity, there is a likelihood that a flow of saliva will be created in conduits and other flow passages connected to the oral appliance to maintain the vacuum. In order to avoid fouling the equipment which produces the vacuum, a saliva collector may be provided in-line to remove and collect the saliva.

SUMMARY

In one aspect, a liquid container for collecting liquid drawn through a vacuum conduit from an oral cavity of a user by a vacuum pump of an oral negative-pressure therapy system is disclosed. The liquid container may include a container body having an interior surface defining an interior space; a fluid inlet for fluidly connecting the vacuum conduit to the interior space; a fluid outlet for fluidly connecting the vacuum pump to the interior space; an interior baffle connected to the container body and disposed in the interior space, the interior baffle configured to support an absorbent insert received thereon; and a fluid passageway extending from the fluid inlet along the interior baffle. The fluid passageway fluidly connects the fluid inlet to the interior space when the absorbent insert is received on the interior baffle.

The interior baffle may include a baffle body and a plurality of baffle standoffs extending outward from the baffle body. The baffle standoffs are configured to space the absorbent insert apart from the baffle body to define fluid flow paths between baffle body and the absorbent insert that are in fluid communication with the fluid passageway and the outlet. At least some of the baffle standoffs of the interior baffle may extend along the baffle body and are spaced apart from one another to define a plurality of flow channels extending along the baffle body. The baffle body may have a connected end connected to the container body and a free end spaced apart from and generally opposing a portion of the interior surface of the container body. At least some of the baffle standoffs of the interior baffle may extend axially outward from the free end of the baffle body to define a plurality of flow channels at the free end of the baffle body.

The container body may include a plurality of body standoffs extending outward from the interior surface of the container body. The body standoffs are configured to space the absorbent insert apart from the interior surface of the container body to define fluid flow paths between the interior surface of the container body and the absorbent insert that are in fluid communication with the fluid passageway and the outlet.

The fluid passageway may extend through the interior baffle. The baffle may have a connected end connected to the container body and a free end spaced apart from and generally opposing a portion of the interior surface of the container body. The fluid passageway may extend through the connected end to the free end of the baffle.

The baffle may have a connected end connected to the container body and a free end spaced apart from and generally opposing a portion of the interior surface of the container body to define a clearance space in which a portion of the absorbent insert is received when the absorbent insert is received on the interior baffle. The container body may have opposite first and second ends and a sidewall extending between the first and second ends. The interior surface of the sidewall may be spaced apart from and surround the baffle to define an annular space in which a portion of the absorbent insert is received when the absorbent insert is received on the interior baffle. The clearance space and the annular space may define a cavity having a U-shaped cross section in which the absorbent insert is received when the absorbent insert is received on the interior baffle.

The interior baffle has an exterior surface defining a plurality of flow channels extending along the interior baffle to define fluid flow paths between the interior baffle and the absorbent insert that are in fluid communication with the fluid passageway and the outlet. The interior baffle may have a sinuous cross-sectional shape defining the plurality of flow channels. The interior baffle may include a baffle body and a plurality of baffle standoffs extending outward from the baffle body to define the plurality of flow channels.

The interior baffle may comprise first and second baffle bodies spaced apart from one another. The fluid passageway may be disposed between the first and second baffle bodies. The container body may include a first body portion and a second body portion removably attachable to the first body portion for opening and closing the container body. The fluid inlet and the baffle may be associated with the first body portion, wherein the outlet is associated with the second body portion.

In another aspect, an absorbent insert for a container of an oral negative pressure therapy system, where the container defines an interior space and including an interior baffle connected to the container body and disposed in the interior space, is disclosed. The absorbent insert may comprises an absorbent pouch having an exterior surface, and an interior surface defining an interior cavity sized and shaped to receive the baffle therein such that the absorbent pouch substantially envelopes the interior baffle.

The absorbent pouch may include a liquid-permeable inner layer defining the interior surface of the absorbent pouch, an outer layer defining the exterior surface of the absorbent pouch. The absorbent pouch may further comprise an absorbent core enveloped between the inner and outer layers. The absorbent core may comprise an absorbent material configured to absorb liquid introduced into the container. The interior surface of the absorbent pouch may include a plurality of formations configured to burst bubbles formed in liquid introduced into the container when the bubbles contact the interior surface of the absorbent pouch.

In another aspect, a method of manufacturing the absorbent insert may comprise providing a liquid permeable inner layer joined to an outer layer to form a two ply construction; folding the two ply construction in substantially half at a midline thereof; and sealing lateral sides of the folded two ply construction to form the absorbent pouch, wherein the liquid permeable inner layer defines the interior surface of the pouch.

In yet another aspect, an oral negative-pressure therapy system generally comprises an oral appliance including an inlet for fluid communication with an oral cavity of a user; a conduit in fluid communication with the inlet of the oral appliance; a negative-pressure pump in fluid communication with the conduit for creating a negative pressure in the oral cavity of the user; a container, as recited above, in fluid communication with the conduit and the negative-pressure pump for collecting liquid drawn through the conduit from the oral cavity of the user by the negative-pressure pump; and an absorbent pouch having an exterior surface and an interior surface defining an interior cavity sized and shaped to receive the baffle therein such that the absorbent pouch substantially envelopes the interior baffle.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

The present disclosure is directed to an oral negative-pressure therapy system, a container for the oral negative-pressure therapy system, and absorbent insert for the container. In one or more embodiments, the oral negative-pressure therapy system may be configured to treat disorders characterized by episodes of complete or partial upper airway obstruction during such as sleep, anesthetization, or post anesthesia, including but not limited to obstructive sleep apnea (OSA), hypopnea, and upper airway resistance syndrome (UARS). A container collects liquid (e.g., saliva) aspirated during use of the oral negative-pressure therapy system. In one or more embodiments, the container includes a baffle inside an interior of the container. In one or more embodiments, a passageway extends along the baffle for delivering fluid (e.g., a mixture of air and saliva) into the container. In one or more embodiments, an absorbent insert for absorbing liquid (e.g., saliva) in the container is received over the baffle. For example, the absorbent insert may comprise a pouch sized and shaped to receive the baffle therein to envelope the baffle. In one or more embodiments, at least one of the baffle and the absorbent insert is configured to maintain a fluid flow path between the baffle and the absorbent insert to maintain fluid communication between a fluid inlet and a fluid outlet of the container. In one or more embodiments, at least one of the container and the absorbent insert is configured to maintain a fluid flow path between the container and the absorbent insert to maintain fluid communication between a fluid inlet and a fluid outlet of the container. In one or more embodiments, the absorbent insert and/or the container is designed and constructed to burst air bubbles in the aspirated liquid. In one or more embodiments, the absorbent insert is replaceable so that a spent absorbent insert can be replaced with a new, fresh absorbent insert.

Figure 1A:
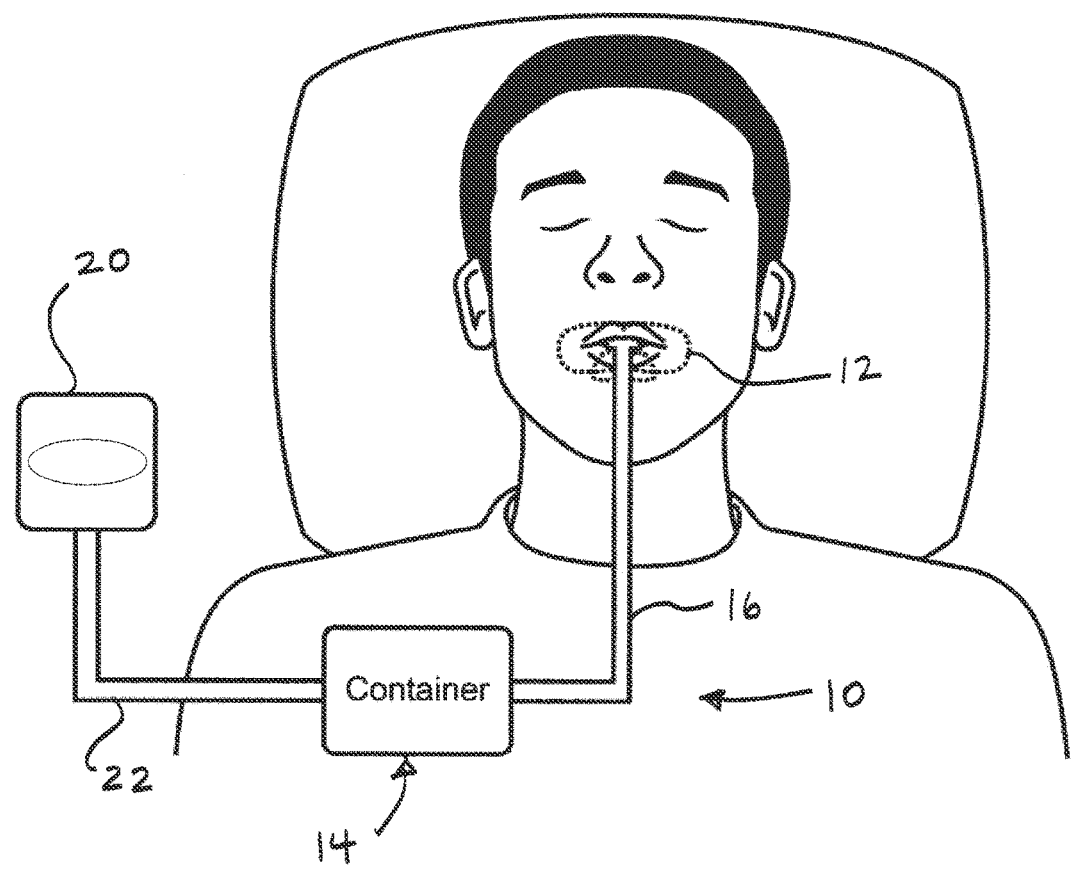
FIG. 1A is a schematic illustrating a person using an embodiment of an oral negative-pressure therapy system comprising an oral appliance delivering negative pressure to an oral cavity of the user, a negative-pressure generator for generating the negative pressure, and a container for collecting liquid aspirated from the oral cavity of the user by the negative-pressure generator.

Referring to FIG. 1, one embodiment of an oral negative-pressure therapy system is generally indicated at reference numeral 10. The oral negative-pressure therapy system 10 is shown during operation, applying a negative pressure to an oral cavity of a user. The illustrated oral negative-pressure therapy system 10 includes an oral appliance 12 configured to fluidly connect the oral cavity of the user with the oral negative-pressure therapy device. The oral appliance 12 is fluidly connected to a liquid container, generally indicated at 14, via an upstream conduit 16, which may be a flexible tube or other device suitable for fluidly connecting the oral appliance to the container. The upstream conduit 16 may be formed integrally with the oral appliance 12. It is understood that the oral appliance 12 may be connected directly to the liquid collector 14, although some conduit defining some passageway would fluidly connect the two. The container 14, in turn, is fluidly connected to a source of negative-pressure 20 (i.e., a negative-pressure generator) via a downstream conduit 22, which may be a flexible tube or other device suitable for fluidly connecting the container to the negative-pressure generator. It is understood that the oral appliance may connected directly to the collector, although some conduit defining some passageway would fluidly connect the two. The source of negative-pressure 20 is configured to pull a partial vacuum within the flow path of the oral negative-pressure therapy system 10, which in turn, generates a partial vacuum within the oral cavity of the user. In one or more embodiments, the source of negative-pressure 20 comprises a vacuum pump (not shown), or other device, for generating suction to pull a partial vacuum within the oral negative-pressure therapy system 10. The source of negative-pressure 20 may include a user interface for controlling the operation of the vacuum pump. The source of negative-pressure 20 may include a controller (e.g., a microcontroller) for operating the vacuum pump. The oral negative-pressure therapy system 10 may be of other overall designs and constructions without departing from the scope of the present invention.

Figure 1B:
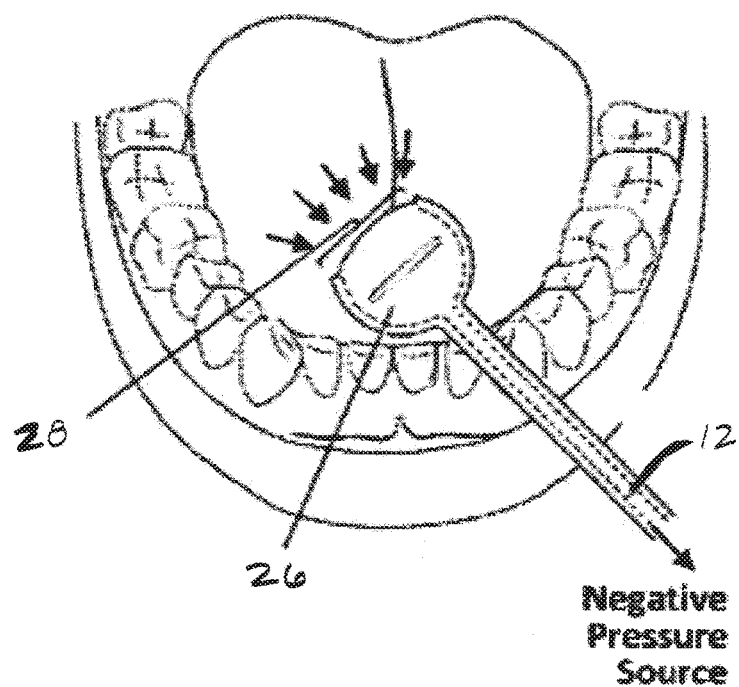
FIG. 1B is a schematic of an oral appliance within a mouth of a user.
Figure 1C:
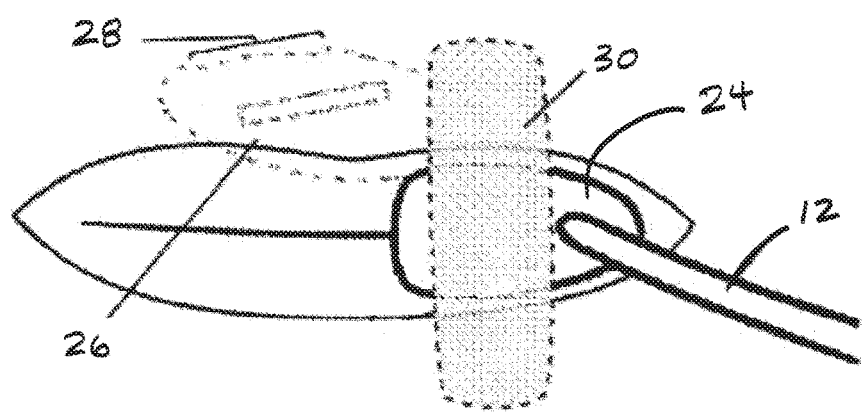
FIG. 1C is a schematic of the oral appliance secured within the mouth of a user.

In the illustrated embodiment, as shown in FIGS. 1B and 1C, the oral appliance 12 includes a mouth piece 24 for connecting the oral appliance to the mouth of the user, and an inlet component 26 defining a fluid inlet 28 configured to be disposed in the oral cavity, in fluid communication therewith. The mouth piece 24 is adhered to the user's mouth using an adhesive strip 30 or in other ways. Suitable oral appliances for the illustrated oral negative-pressure therapy device 10 are disclosed in co-pending U.S. application Ser. No. 13/958,159, filed Aug. 2, 2013, Ser. No. 12/891,398, filed Sep. 27, 2010, and Ser. No. 14/760,429, filed Jul. 10, 2015, the entirety of each of which is hereby incorporated by reference. The oral appliance may be of other types and/or configurations without departing from the scope of the present invention.

Figure 2:
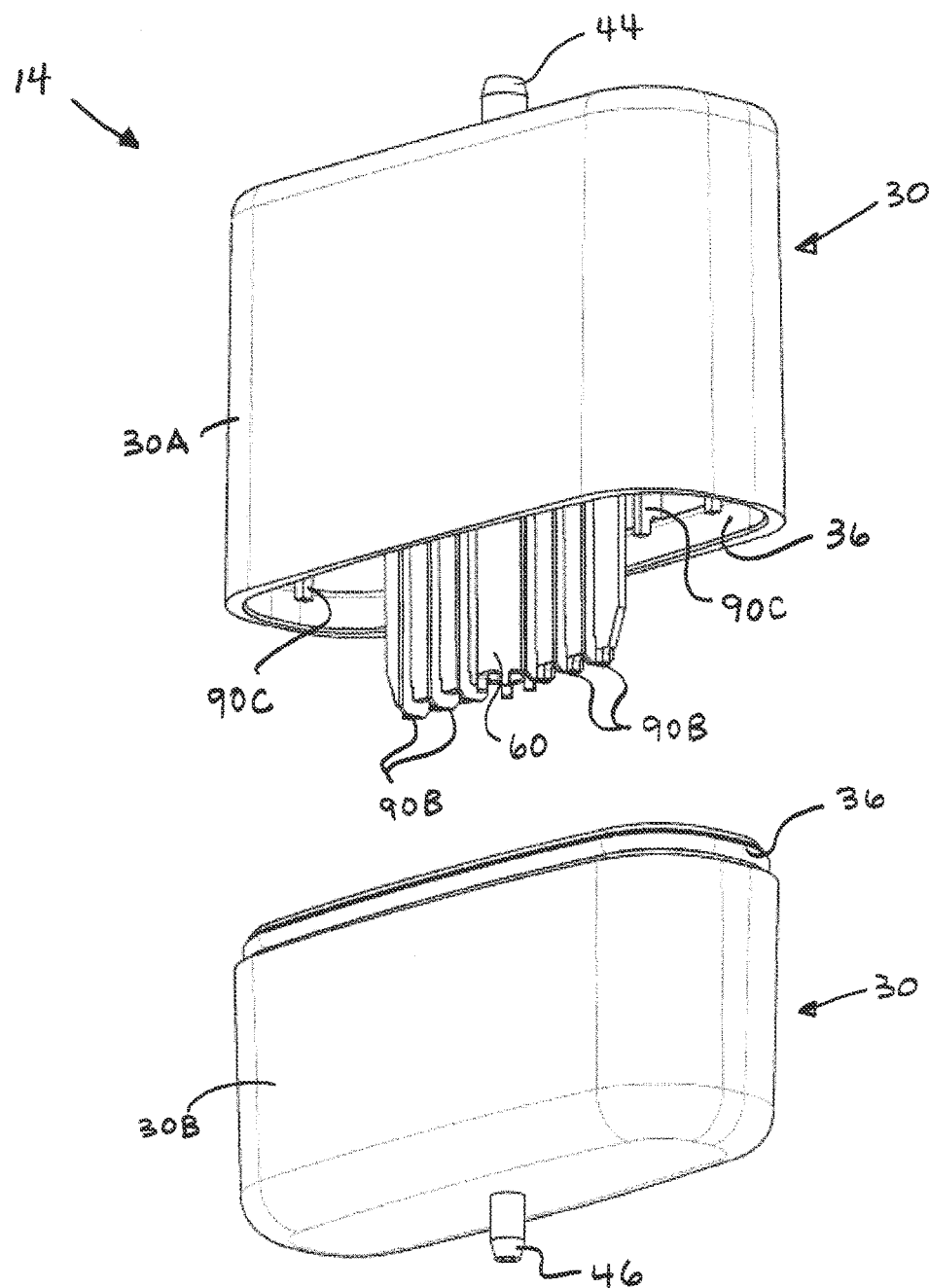
FIG. 2 is an exploded view of one embodiment of the container, with first and second container body portions separated from one another to open the container.
Figure 3:
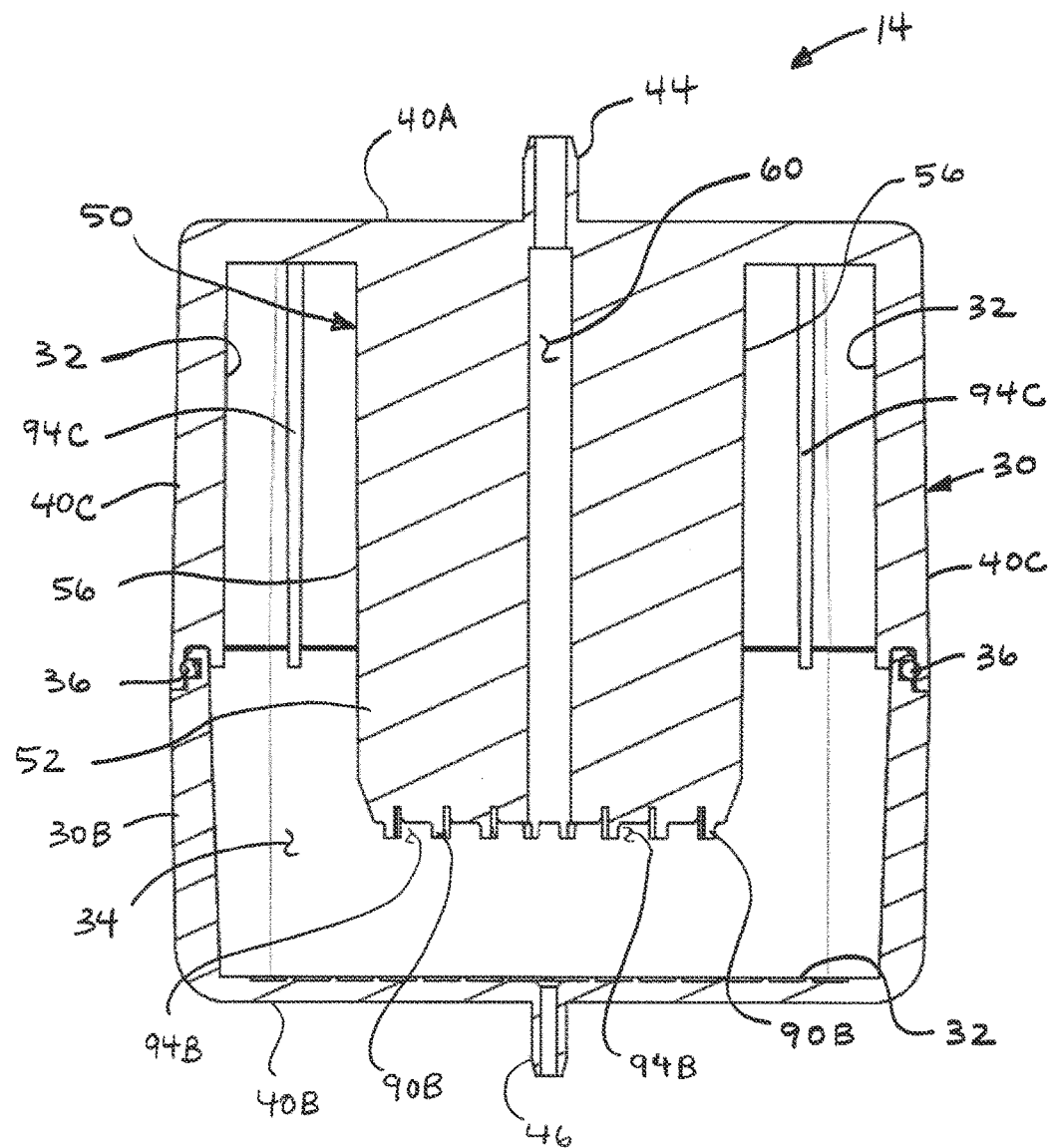
FIG. 3 is a sectional view of the container taken in a plane defined by the axis A.
Figure 4:
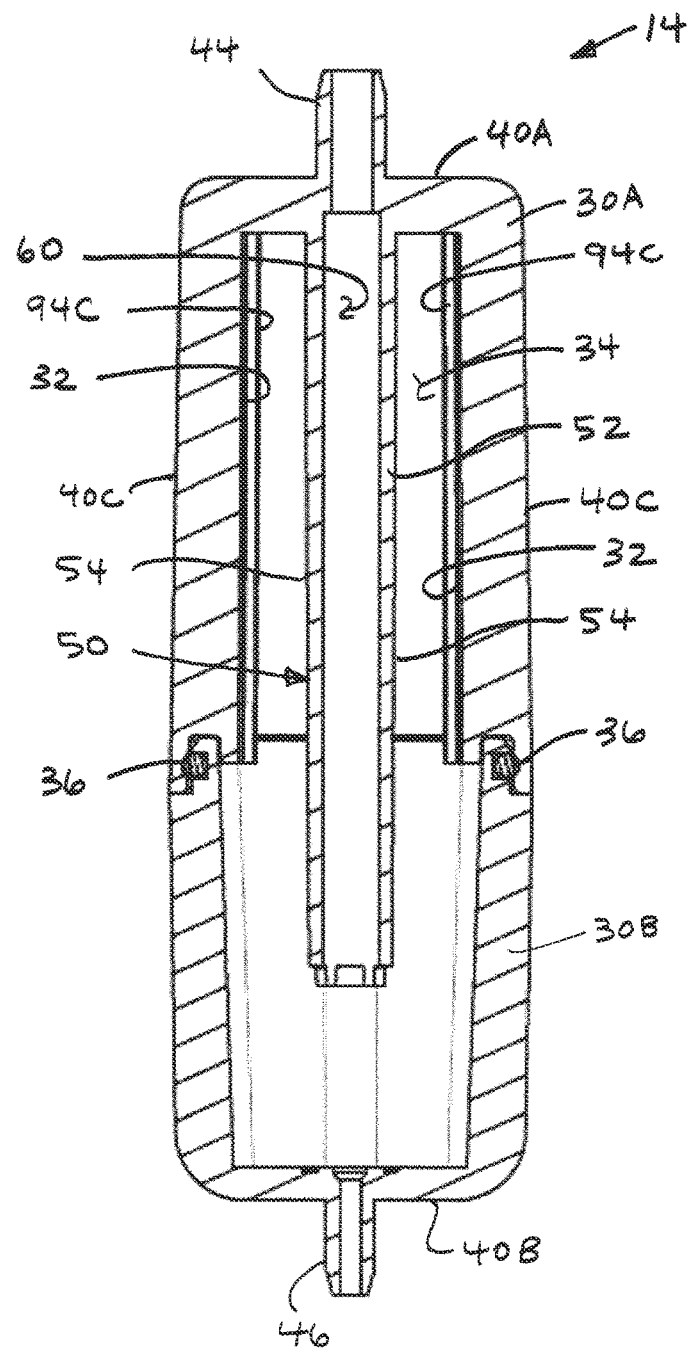
FIG. 4 is a sectional view of the container taken in a plane offset 90 degrees about the axis A relative to the plane of FIG. 3.

Referring to FIGS. 2-4, the liquid container 14 comprises a container body, generally indicated at 30, having an interior surface 32 defining an interior space 34. The interior space 34 is enclosed by the container body 30. In the illustrated embodiment, the container body 30 includes first and second body portions 30A, 30B that are removably attachable to one another to open and close the container body. The first and second body portions 30A, 30B may be removably attachable to one another by friction fit connection, snap-fit connection, or other mechanical connections. In the illustrated embodiment, at least one of the body portions 30A, 30B (e.g., both body portions) includes a seal 36 (e.g., a gasket or O-ring) for forming a fluid-tight seal at the juncture of the first and second body portions. Referring to FIGS. 3 and 4, the illustrated container body 30 has opposite first and second end walls 40A, 40B, respectively, and a sidewall 40C extending between and interconnecting the first and second end walls. The first body portion 30A includes the first end wall 40A and a first longitudinal portion of the sidewall 40C, and the second body portion 30B include the second end wall 40B and a second longitudinal portion of the sidewall 40C. The container body 30 may be formed from generally rigid plastic, such as polypropylene (PP), polycarbonate (PC), acrylonitrile butadiene styrene (ABS), or other material. Suitably, the container body 30 is designed and constructed to inhibit collapsing when the negative pressure is applied by the source of negative pressure 22. Each of the container body portions 30A, 30B may be formed by injection molding process or in other ways.

The liquid container 14 includes a fluid inlet 44 and a fluid outlet 46, each of which are in fluid communication with the interior space 34 of the container body 30 and one another. The fluid inlet 44 fluidly connects the upstream conduit 16 to the interior space 34 of the container body 30, and the fluid outlet 46 fluidly connects interior space of the container body to the downstream conduit 22. In the illustrated embodiment, each of the fluid inlet 44 and fluid outlet 46 are configured as connectors for physical connection to the respective upstream and downstream conduits 16, 22, respectively. In particular, the illustrated fluid inlet 44 and fluid outlet 46 comprise male connectors suitable for reception in and connection to fluid tubing. In other embodiments, one or both of the fluid inlet and fluid outlet may comprise female connectors suitable for receiving male connector associated with the respective upstream and downstream conduits 16, 22, respectively. It is understood that in one or more other embodiments, the fluid inlet 44 and/or the fluid outlet 46 may not be configured for physical connection to the respective upstream and downstream conduits 16, 22, respectively, but instead, may only be suitable for fluidly connecting to the corresponding one of the upstream and downstream conduits. In the illustrated embodiment, the fluid inlet 44 is associated with the first container body portion 30A, and the fluid outlet 46 is associated with the second container body portion 30B.

An interior baffle, generally indicated at reference numeral 50, is connected to the container body 30 and disposed in the interior space 34 of the container body. In the illustrated embodiment, the baffle 50 is connected to the first end wall 40A of the container body 30. In other embodiments, the baffle 50 may be disposed at other locations. The baffle 50 includes a baffle body 52 having a generally planar (i.e., thin) rectangular shape, although the baffle may have other shapes. Opposite broad sides 54 (FIG. 4) and opposite thin sides 56 (FIG. 3) extend along a length of the baffle body 52 from a connected first end to a free second end of the baffle body. The broad and thin sides 54, 56, respectively, are spaced apart radially from the interior surface 32 of the side wall 40C of the container body 30 to define an annular portion of the interior space 34 therebetween. The first end of the baffle body 52 is connected to (e.g., integrally formed with) the container body 30. The second end of the baffle body 52 opposes and is spaced apart from a portion (e.g., the second end wall 40B) of the interior surface 32 of the container body 30 to define an end portion of the interior space 34 therebetween. As shown in FIG. 3 and for reasons explained below, the annular space and the end space together define an absorbent insert-receiving cavity having a generally U-shaped cross section.

Referring to FIGS. 3 and 4, a fluid passageway 60 is in fluid communication with the fluid inlet 44 and extends along (i.e., lengthwise of) the baffle 50. The fluid passageway 60 fluidly connects the fluid inlet 44 with the interior space 34 of the container body 30. In the illustrated embodiment, the fluid passageway 60 extends through the baffle body 52. In one or more embodiments, the fluid passageway 60 extends from the connected first end through the free second end of the baffle body 52. The fluid passageway 60 may be defined by the baffle body 52, or the fluid passageway may be a separate conduit extending along the baffle body, either inside or outside the baffle body. In the illustrated embodiment, the fluid passageway 60 is axially aligned with the fluid inlet 44 and the fluid outlet 46, although in other embodiments the axes may not be aligned.

Figure 5A:
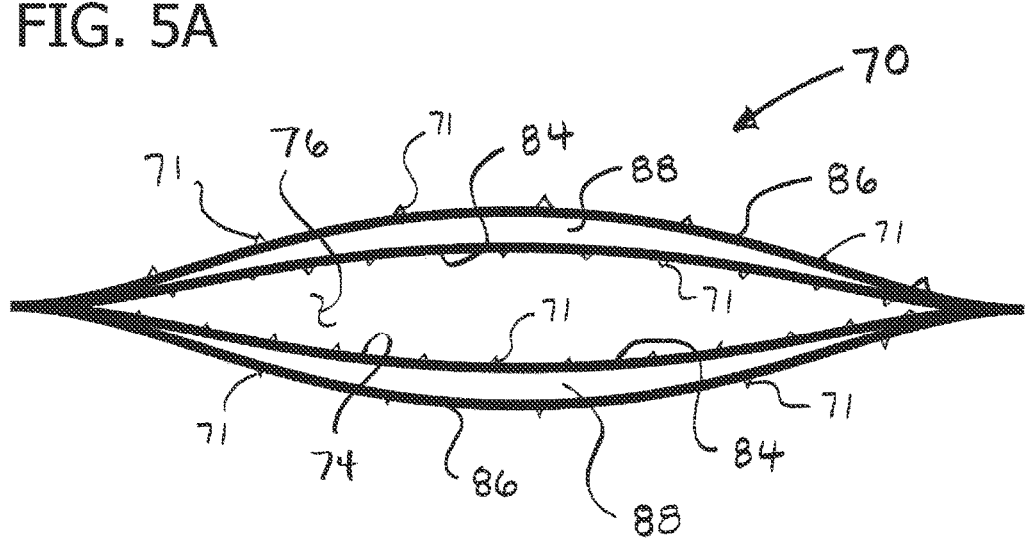
FIG. 5A is an embodiment of an absorbent insert for the container including an absorbent pouch.
Figure 6:
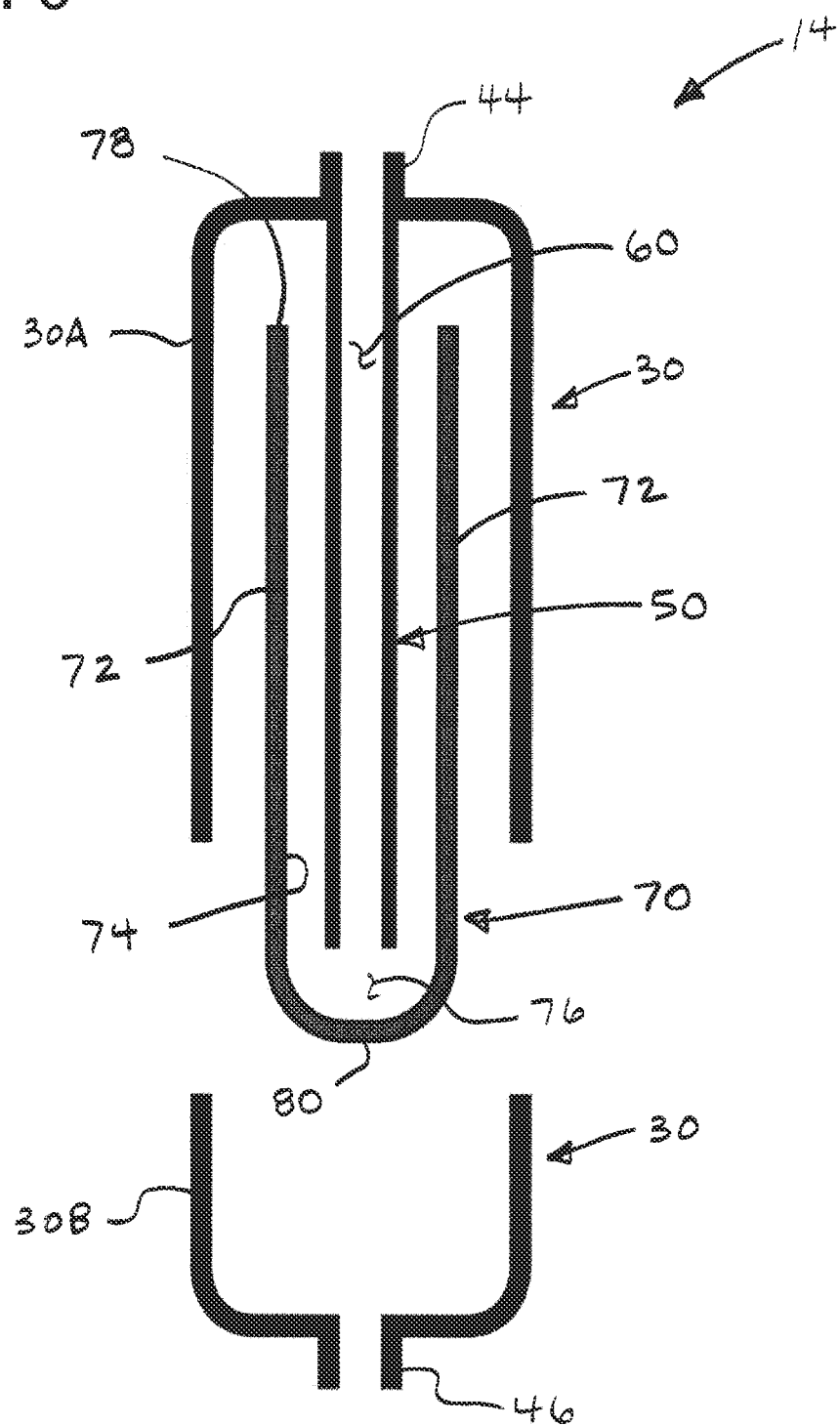
FIG. 6 is a schematic sectional view similar to FIG. 4, except with the first and second container body portions separated from one another and the absorbent insert of FIG. 5A received on an interior baffle of the container.
Figure 7:
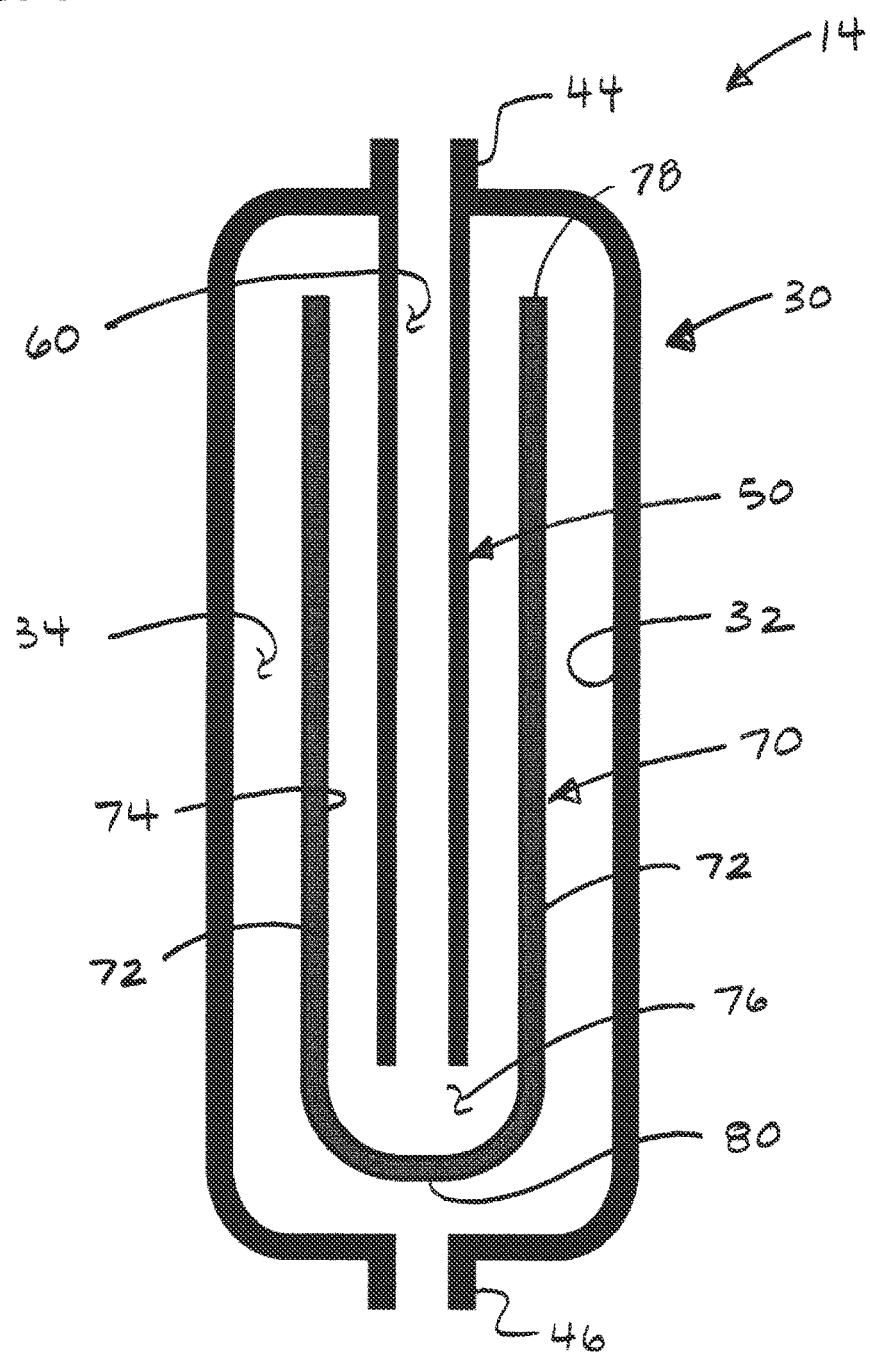
FIG. 7 is similar to FIG. 6, except with the first and second container body portions connected to one another to close the container.

Referring to FIGS. 6 and 7, an absorbent insert, generally indicated at reference numeral 70, is receivable in the interior space 34 of the container body 30. The absorbent insert 70 is configured to absorb liquid (e.g., saliva) aspirated into the container 14 during use. In one embodiment, the absorbent insert 70 comprises an absorbent pouch for receiving the interior baffle 52 such that the absorbent insert substantially envelopes the baffle. The absorbent pouch has a sidewall 72 having an interior surface 74 defining a cavity 76 in which the baffle 50 is received, an open end 78 leading to the cavity, and a closed end 80. Referring to FIG. 5A, in one embodiment, the absorbent insert 70 includes an inner layer 84 defining the interior surface 74 defining the cavity 76, an outer layer 86 defining an exterior surface of the insert, and an absorbent core 88 disposed (e.g., enveloped) between the inner and outer layers. As shown in FIGS. 6 and 7, the container body 30 may be opened to insert the absorbent insert 70 onto the baffle 50. The container body 30 may then be closed by connecting the first and second body portions 30A, 30B to one another. The first and second body portions 30A, 30B may also be separated to remove/replace the absorbent insert 50.

Figure 18:
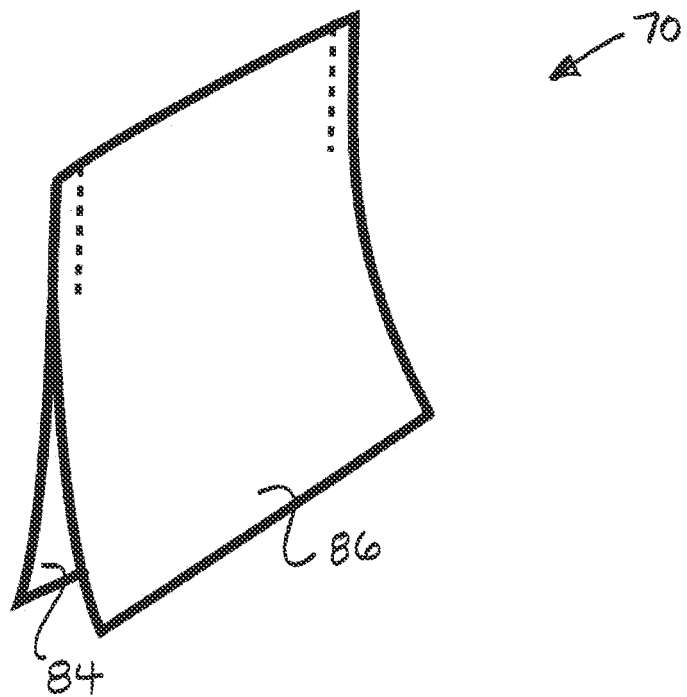
FIG. 18 is a perspective of one embodiment of the absorbent insert.
Figure 19:
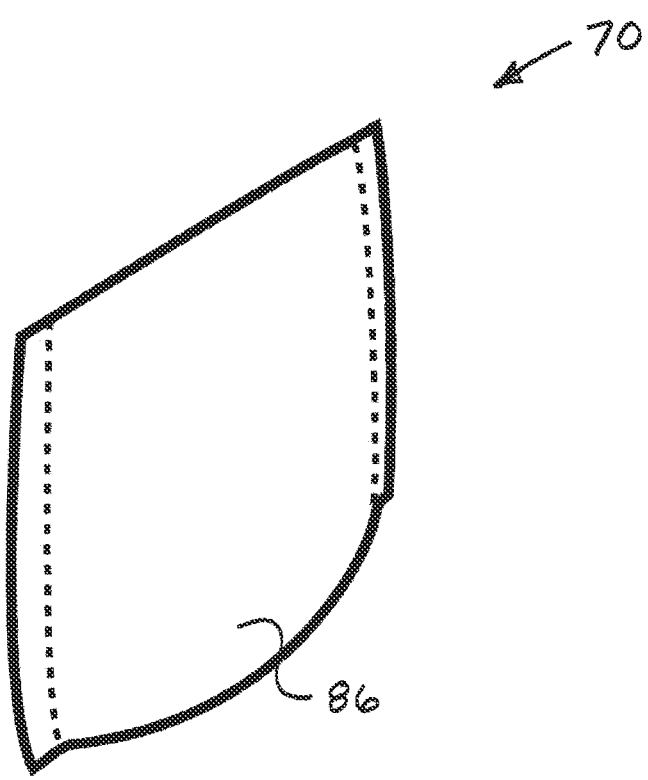
FIG. 19 is a perspective illustrating the formation of the absorbent insert embodiment of FIG. 18.
Figure 20:
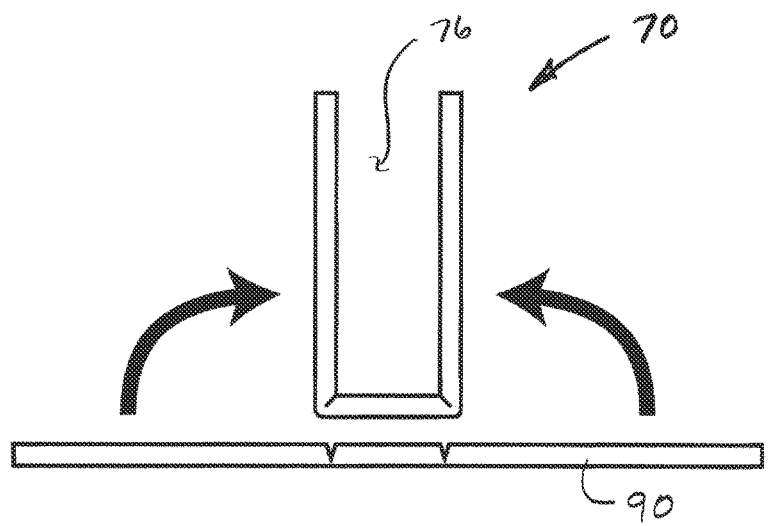
FIG. 20 is a schematic illustrating the folding of an embodiment of the absorbent insert.
Figure 21:
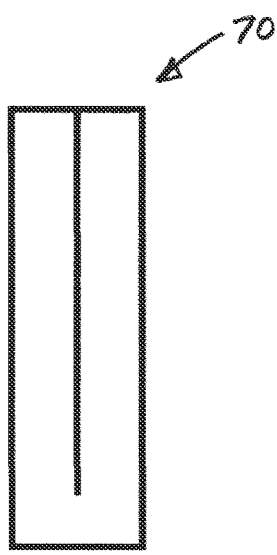
FIG. 21 is a front elevation of the absorbent insert formed in FIG. 20.
Figure 22:
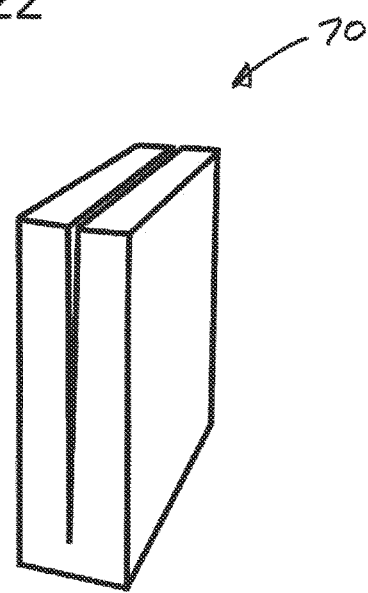
FIG. 22 is a perspective of the absorbent insert of FIG. 21.

As shown in FIGS. 18-20, the absorbent insert 70 may be manufactured from a sheet of material 90 (FIG. 20) comprising the inner layer 84, the outer layer 86, and the absorbent core 88. As shown in FIG. 20, the sheet of material 90 may be folded upon itself, and then opposing sides of the folded sheet may be sewn, adhered or otherwise secured to one another to form the pouch, as shown in FIGS. 18 and 19. In other embodiments, the absorbent insert may not comprise an enclosed pouch. Instead, as shown in FIGS. 21-22, the sheet may be folded upon itself and the sides may be left unsecured to one another. The absorbent insert 70 may be of other shapes and configurations without departing from the scope of the present invention.

Figure 25:
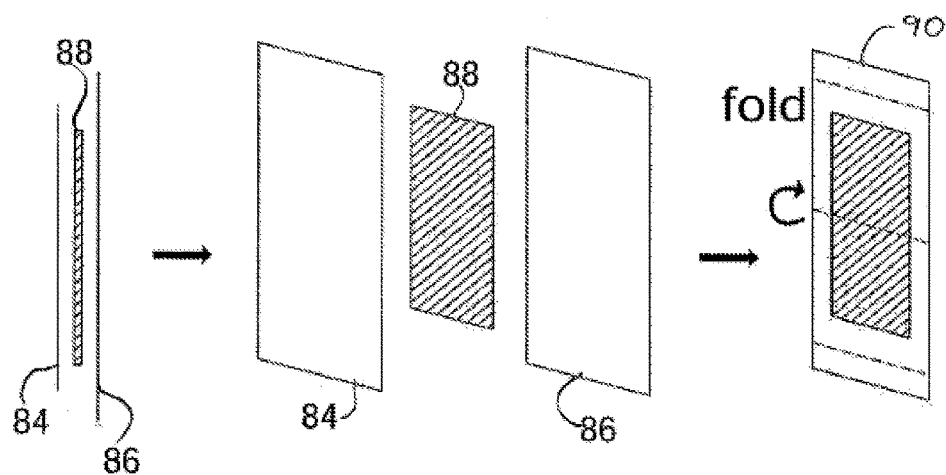
FIG. 25 is a schematic illustrating the folding of another embodiment of the absorbent insert.
Figure 25:
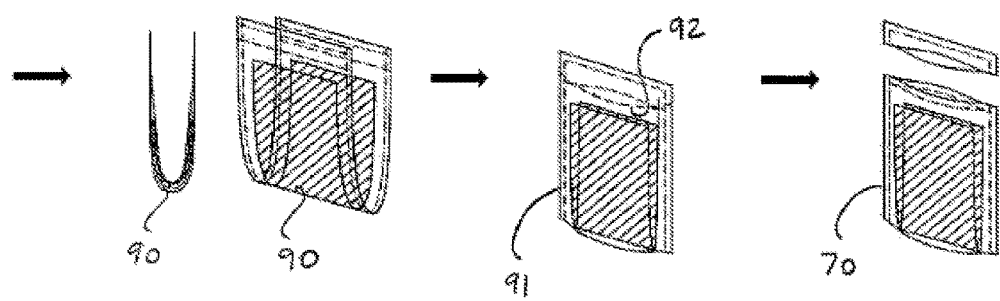

FIG. 25 illustrates another embodiment of making the absorbent insert 70. Similar to the embodiment in FIGS. 18-20, the absorbent insert 70 is made from a sheet of material 90. The sheet of material 90 is formed by sandwiching the absorbent core 88 between the inner and outer layers 84, 86. The inner and outer layers 84, 86 are secured to one another along respective perimeters to form a two ply construction. The sheet of absorbent material 90 is folded upon itself (i.e., folded substantially in half at a midline) and secured along its lateral edges to form an enclosed pack 91. The side opposite the midline may also be secured. The end portion of the pack opposite to the folded end (i.e., midline) is tearable to form the pouch suitable for receiving the baffle. The end of the pack 91 may include perforations 91 or otherwise formed with a line of weakness to facilitate removable of the end portion to form the pouch 70 before use. The enclosed pack is hygienic and easy to use.

In one or more embodiments, the inner layer 84 is liquid permeable to allow liquid to flow (e.g., permeate) through the inner layer to the absorbent core 88. One suitable permeable material from which the inner layer 84 may be constructed is a polypropylene or polyethylene film having apertures formed therein to permit liquid (e.g., saliva) to flow therethrough. The inner layer 84 may be formed from fiber, cloth, film, web (nonwoven), foam, or a sheet of material, for example. In one or more embodiments, the inner layer 84 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and non-woven fabrics can be used for the inner layer 84. For example, the inner layer 84 can be composed of a meltblown or spunbonded web of polyolefin fibers. Alternatively, the inner layer 84 can be a bonded-carded web composed of natural and/or synthetic fibers. The inner layer 84 can also be composed of a substantially hydrophobic material, and the hydrophobic material can, optionally, be treated with a surfactant or otherwise processed to impart a desired level of wetability and hydrophilicity.

In one or more embodiments, the outer layer 86 is liquid permeable to allow liquid to flow (e.g., permeate) through the outer layer to the absorbent core 88. Suitable materials may be the same as the materials for the inner layer 84. In one or more other embodiments, the outer layer 86 is liquid impermeable to inhibit liquid absorbed by the absorbent core 88 from leaking out the absorbent insert. The outer layer 86 may be formed from thin plastic film, such as a polyethylene or polypropylene film.

The absorbent core 88 is capable of absorbing and retaining liquid, such as saliva. The absorbent core 88 may comprise hydrophilic fibers and/or a high-absorbency material commonly known as superabsorbent material, including by not limited to material comprising polyvinyl alcohol (PVA) (e.g., PVA fibers and/or hydrogels). More particularly, the absorbent core 88 may have a first layer composed of cellulosic fluff, such as wood pulp fluff, and a second layer desirably composed of superabsorbent hydrogel-forming particles, or a mixture of cellulosic fluff and superabsorbent hydrogel-forming particles. In another embodiment, the absorbent core 88 may be a single layer composed of a mixture of hydrophilic fibers and superabsorbent material. It is also contemplated that the absorbent may 88 be composed solely of superabsorbent material without departing from the scope of this invention. The wood pulp fluff can be exchanged with other hydrophilic fiber materials, such as synthetic, polymeric, or meltblown fibers or with a combination of meltblown fibers and natural fibers. Suitable superabsorbent materials can be selected from natural, synthetic, and modified natural polymers and materials. The superabsorbent materials can be inorganic materials, such as silica gels, or organic compounds, such as cross-linked polymers.

Figure 8:
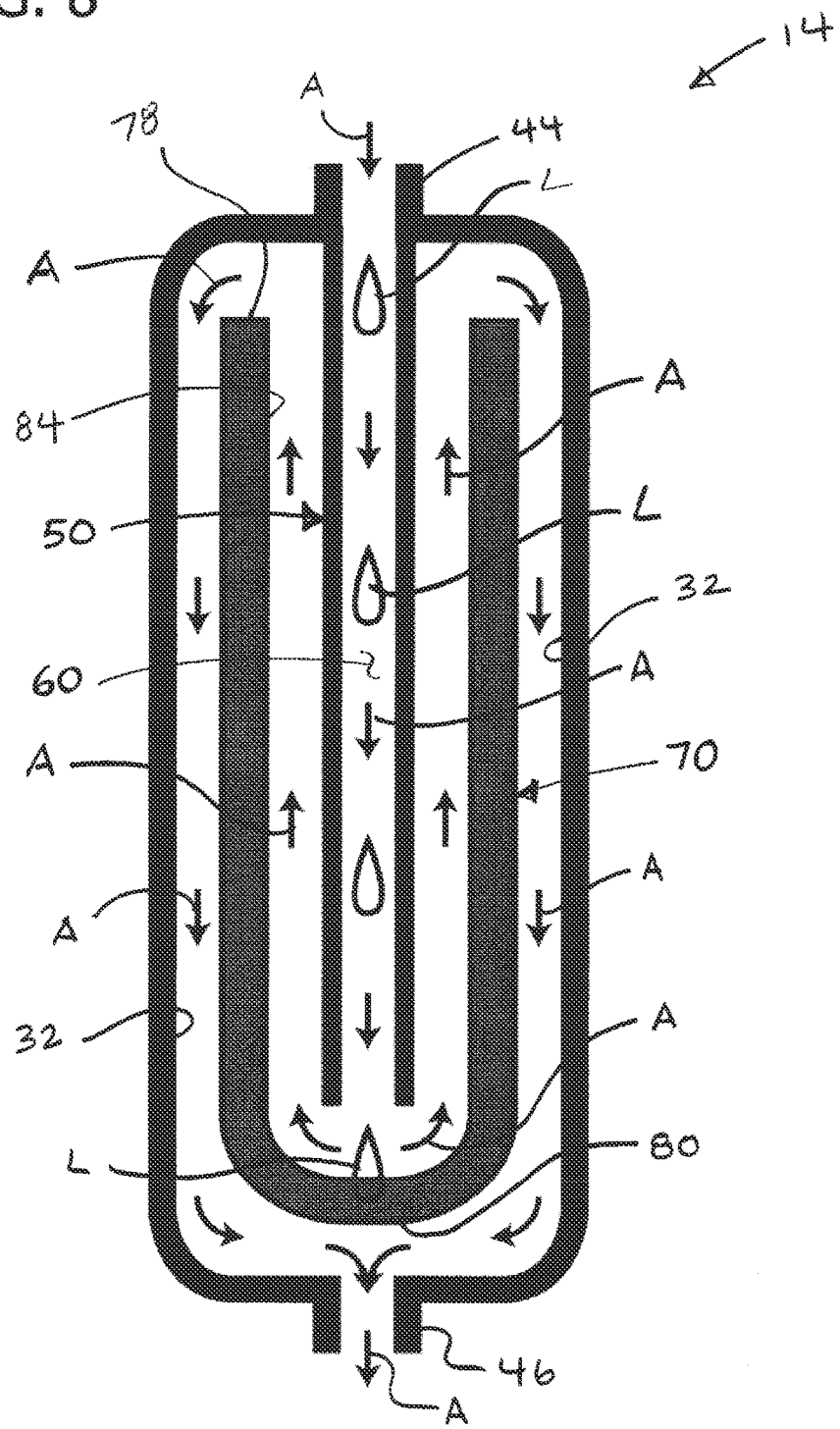
FIG. 8 is a schematic similar to FIG. 7, except showing liquid and gas entering the container, with liquid being absorbed by the absorbent insert and gas exiting the container.

Referring to FIG. 8, during use fluid (e.g., a mixture of saliva, indicated by drop L, and air, indicated by arrows A, from the oral cavity) flows through the fluid inlet 44 and into and through the fluid passageway 60. The fluid exits the fluid passageway 60 adjacent the closed end 80 of the absorbent insert 70. At least some of the liquid L exiting the fluid passageway 60 may be absorbed by the absorbent insert 70 at its closed end 80. Gas A (e.g., air) that exited the fluid passageway 60 flows in a first fluid path defined between the baffle body 52 and the interior surface 84 of the absorbent insert 70. The fluid flow in the first fluid path is in a direction opposite its flow in the fluid passageway 60. Any liquid L that is entrained in the gas A or otherwise moves along the first fluid flow path may be absorbed by the absorbent insert 70 as it moves along the first fluid path. It is envisioned that most of the liquid L will be absorbed as it exits the fluid passageway 60 adjacent the close end 80 or otherwise within the first fluid path. The gas A exits the first fluid path at the open end 78 of absorbent insert 70, and then flows within a second fluid path defined between the exterior surface of the absorbent insert and the interior surface 32 of the container body 30. The flow of fluid in the second fluid path is in a direction opposite its flow in the first fluid path. In one or more embodiments, where the outer layer 86 of the absorbent insert is liquid permeable, any liquid L that is entrained in the gas A or otherwise present in the second fluid flow path may be absorbed by the absorbent insert 70 as it flows in the second fluid path. In other embodiments, the outer layer 86 is liquid impermeable, and liquid L in the second flow path is not absorbed by the absorbent insert 70. The fluid flows from the second fluid path into the fluid outlet 46 and toward the source of negative pressure 20.

In one or more embodiments, at least one of the liquid container 14 and the absorbent insert 70 are configured to maintain fluid communication between the fluid passageway 60 (and thus the fluid inlet 44) and the fluid outlet 46 within the container body 30 during use of the system 10. In other words, at least one of the container 14 and the absorbent insert 70 may be designed and constructed to maintain the flow of gas from the fluid passageway 60, along the first and second fluid paths to the fluid outlet 46 during operation of the system 10.

Figure 11:
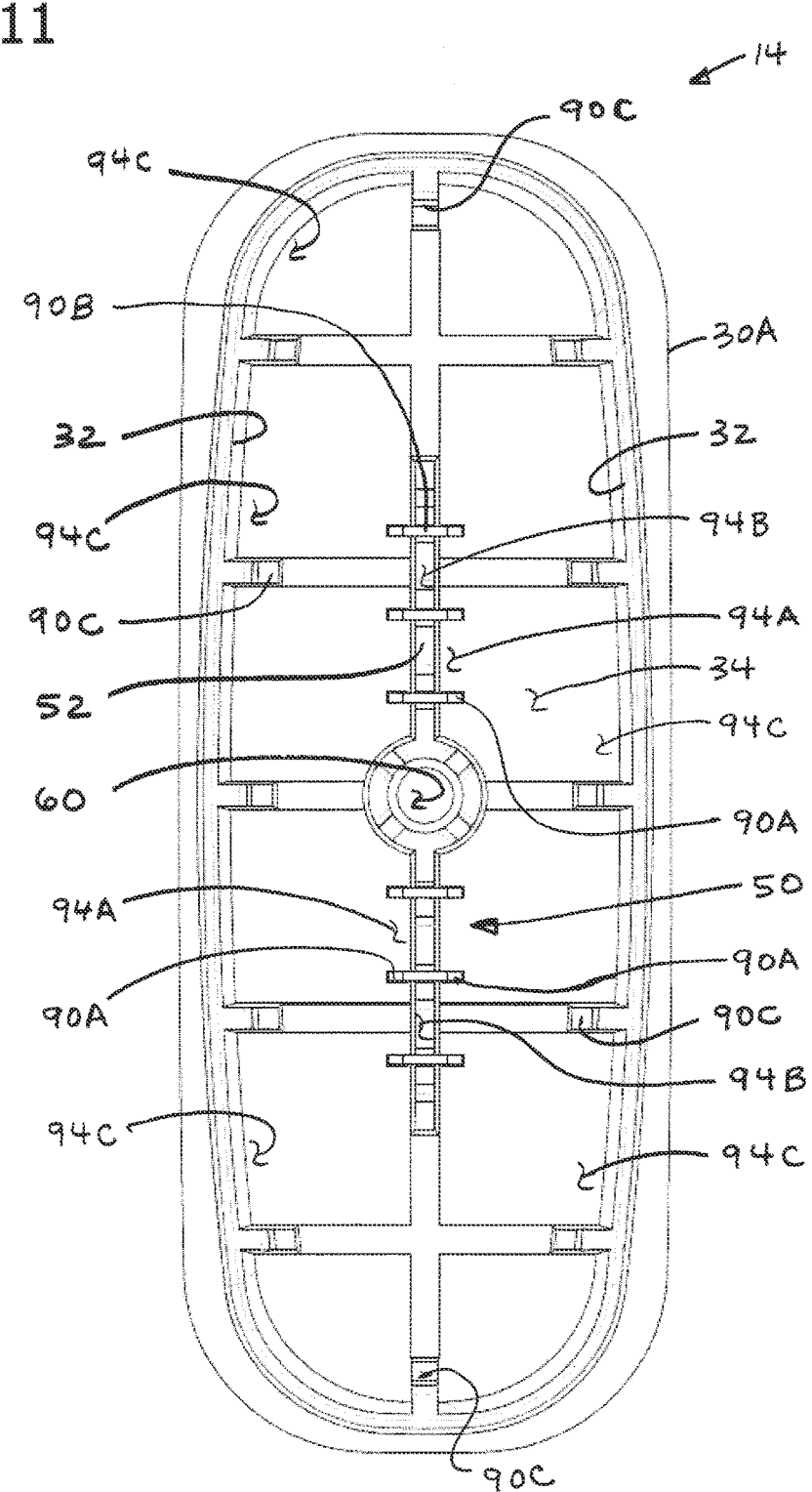
FIG. 11 is a bottom plan view of the first container body portion of the container embodiment shown in FIG. 2 including standoffs on an interior baffle and an interior surface of the container.

In one example, at least the container 14 is configured to maintain fluid communication between the fluid passageway 60 (and thus the fluid inlet 44) and the fluid outlet 46 within the container body 30 during use of the system 10. In one or more embodiments, the container 14 includes structure designed and constructed to maintain a space between the surfaces of the container within the interior space 34 of the container body 30 to maintain the patency of the fluid path(s). In one example the container 14 includes standoffs in the interior space 34 of the container body 14. Referring to FIG. 11, in this illustrated embodiment standoffs 90A, 90B, 90C are provided on both the baffle body 52 and the interior surface 32 of the container body 30. In one or more other embodiments, standoffs may be provided on only one (or neither) of the interior baffle 50 and the interior surface 32 of the container body 30.

Referring to the interior baffle 50 shown in FIGS. 2 and 11, at least some standoffs 90A may project laterally outward from and extend along the length of the baffle body 52. In particular, these standoffs 90A extend from the broad sides 54 of the baffle body 52. As shown in FIGS. 2, 3 and 11, at least some of the standoffs 90B may project axially outward from the free end of the baffle body 52. The illustrated standoffs 90A, 90B comprise ribs spaced apart from one another in a direction transverse to the length of the baffle body 52 such that adjacent standoffs define a plurality of flow channels 94A, 94B, respectively (FIGS. 3 and 11). The flow channels 94A, 94B defined by the standoffs 90A, 90B, respectively—which together define at least a portion of the first fluid path—are in fluid communication with the outlet of the fluid passageway 60 and the fluid outlet 46. During use, when the absorbent insert 70 is received on the baffle 50, the standoffs 90A, 90B maintain spacing between the baffle body 52 and the interior surface 74 of the absorbent insert 70 to maintain the patency of the flow channels, even during the expansion of the absorbent insert as it absorbs liquid.

Figure 14:
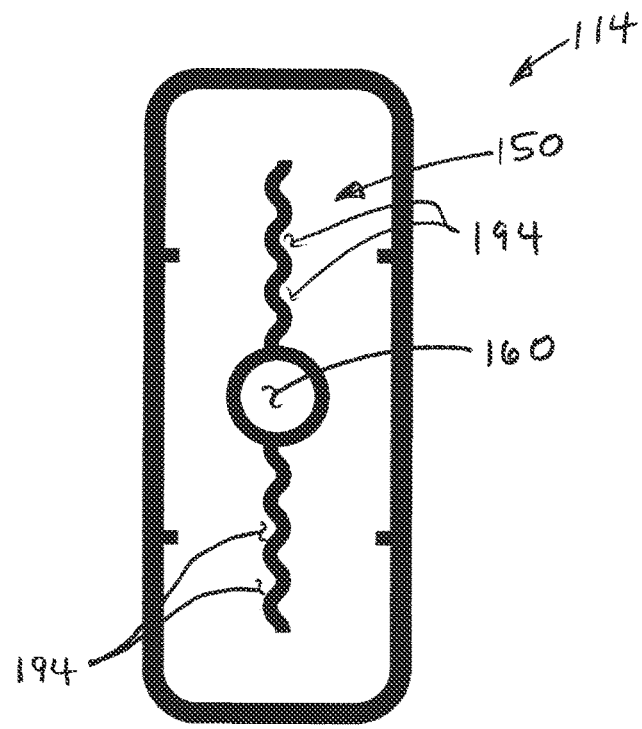
FIG. 14 is a schematic bottom plan view of a first container body portion of another embodiment of the container similar to the first container body portion of FIG. 13, except the container includes standoffs and the interior baffle has a sinuous cross section.

In another embodiment shown in FIG. 14, the container 114 includes an interior baffle 150 having a sinuous cross-sectional shape defining a plurality of flow channels 194 which together define at least a portion of the first fluid path and are in fluid communication with the outlet of the fluid passageway 160 and the fluid outlet (not shown). The sinuous shape of the interior baffle 150 maintains patency of the fluid flow path. The interior baffle 150 may be of other shapes and other configurations for maintaining the patency of the fluid flow path. Other teachings of the container 14 set forth above may apply equally to the container 114.

Referring to FIGS. 3 and 11, the container body 30 includes at least some standoffs 94C extending outward from the interior surface 32 of the container body 30. The illustrated standoffs 90C comprise ribs spaced apart from the one another around the interior baffle 50 such that adjacent standoffs define a plurality of flow channels 94C. The flow channels 94C defined by the standoffs 90C—which together define at least a portion of the second fluid path—are in fluid communication with the first fluid flow path and the fluid outlet 46. During use, when the absorbent insert 70 is received on the baffle 50, the standoffs 90C maintain spacing between the interior surface 32 of the container body 30 and the exterior surface of the absorbent insert to maintain the patency of the flow channels even during the expansion of the absorbent insert as it absorbs liquid. In one or more other embodiments, the standoffs 90C may be of other designs and configurations to maintain the patency of the flow paths through the container body 30.

Figure 5B:
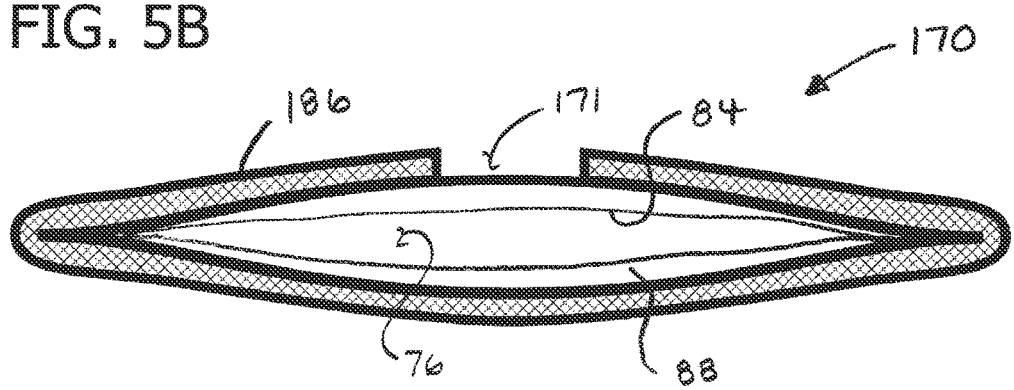
FIG. 5B is another embodiment of the absorbent insert.
Figure 5C:
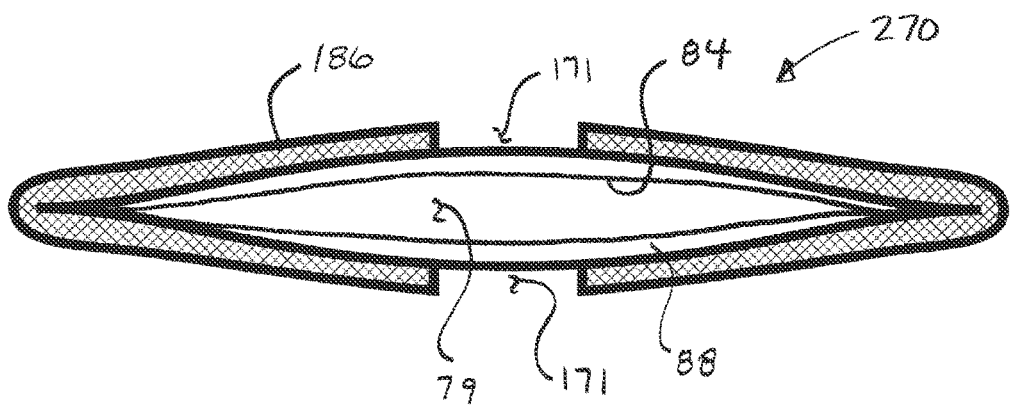
FIG. 5C is yet another embodiment of the absorbent insert.

In one or more embodiments the absorbent insert may include structure that is designed and constructed to maintain a space(s) between the absorbent insert and the surfaces of the container body within the interior space 34 of the container body 30 to maintain the patency of at least one of the first and second fluid paths. For example, one or more embodiments of the absorbent insert may define a crease or groove defining a fluid flow channel. For example, one or more fluid flow channels may be defined on an exterior of the absorbent insert to maintain the patency of the second fluid flow path, and/or one or more fluid flow channels may be defined on the interior of the absorbent insert to maintain the patency of the first fluid flow path. The one or more fluid flow channels may extend along the length of the absorbent insert. In the example shown in FIG. 5B, the outer layer 186 defines a fluid flow channel 171. In the example shown in FIG. 5C, the outer layer 186 defines two fluid flow channels 171. In one or more embodiments, the inner layer and/or the outer layer may be formed from a 3D mesh material. In FIGS. 5B and 5C, the outer layer 186 is formed from a 3D mesh material. In such an example, as the absorbent core 88 expands due to absorbing the liquid, the absorbent core protrudes through openings in the 3D mesh, which creates fluid flow channels along the absorbent insert 70. The absorbent insert may include other structure to define fluid flow channels or grooves.

Referring to FIG. 5A, in one or more embodiments, at least one of the interior surface 74 and the exterior surface of the absorbent insert 70 may be designed and constructed to burst air bubbles formed in liquid that contacts the absorbent insert. Air bubbles formed in the liquid (e.g., saliva) may block or restrict the flow of fluid within the container 14 to the fluid outlet 46. At least one of the interior surface 74 and the exterior surface of the absorbent insert 70 may include projections 71 defined by a rough texture, fibers, or other structures that burst air bubbles when the bubbles come in contact with the surface of the absorbent insert. In one or more other embodiments, surfaces of the container 14 within the interior space 34—such as the interior surface 32, surfaces of the baffle 50, and surfaces of the standoffs 90A, 90B, 90C—may be designed and constructed to burst air bubbles formed in liquid that contacts the surface of the container. One or more surfaces may be formed with projections defined by a rough texture or other projections.

Figure 26:
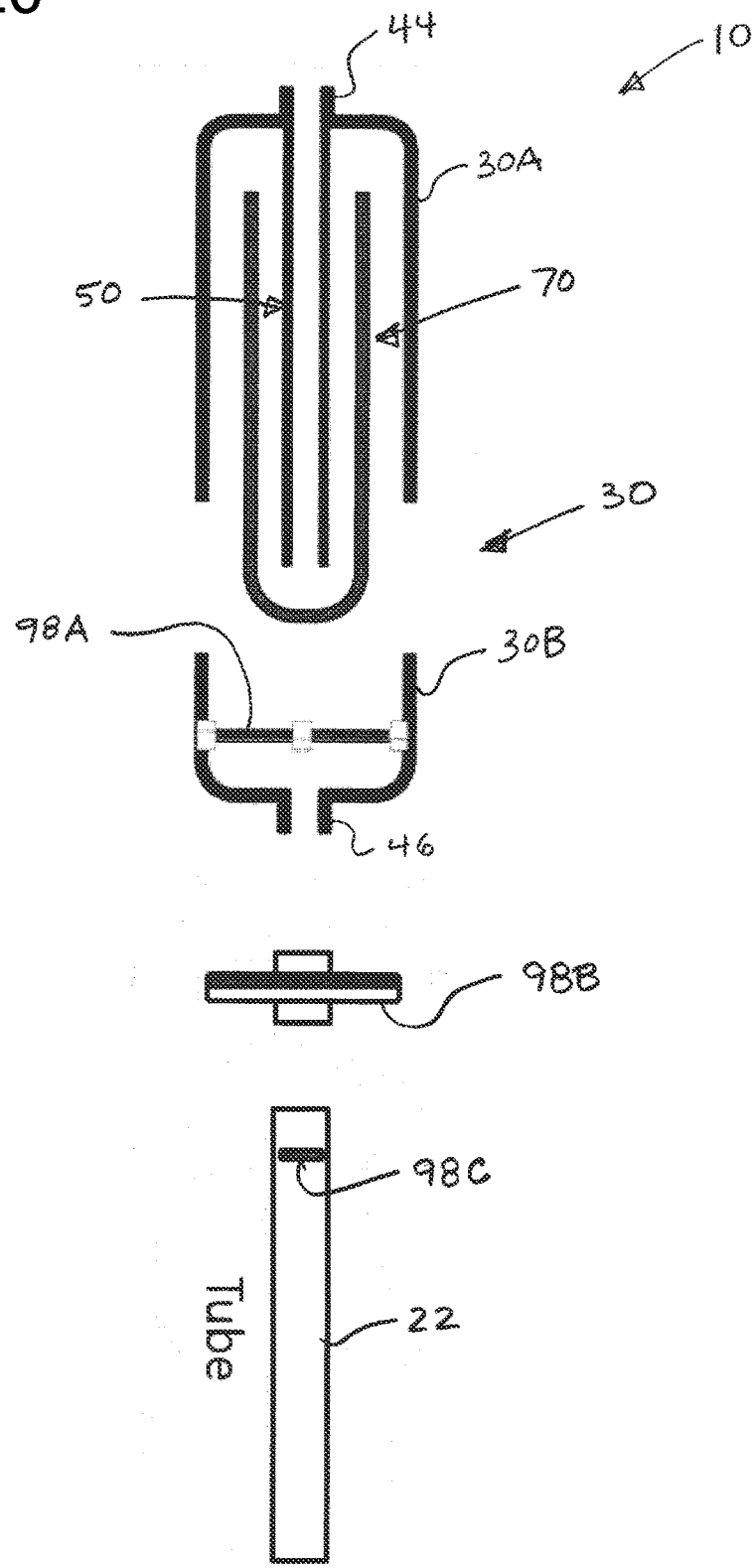
FIG. 26 is schematic of another embodiment of a container, including a filter and conduit removed from the container.

Referring to FIG. 26, in one or more embodiments the oral negative-pressure therapy system 10 may include at least one liquid-impermeable, gas permeable filter to inhibit liquid (e.g., saliva) that has not been absorbed by the absorbent insert 70 from entering the source of negative pressure 20. FIG. 26 illustrates three possible locations for one or more filters. A first filter 98A is placed within the interior space 34 of the container body 30 adjacent the fluid outlet 46. A second filter 98B is placed between the fluid outlet 46 and the downstream conduit 22 leading to the source of negative pressure 20. This second filter 98B may also be suitable for interconnecting the fluid outlet 46 of the container 14 and the downstream conduit 22. A third filter 98C is placed within the downstream conduit 22. A liquid-impermeable, gas permeable filter may be of other configurations and in other locations of the system 10.

Figure 15:
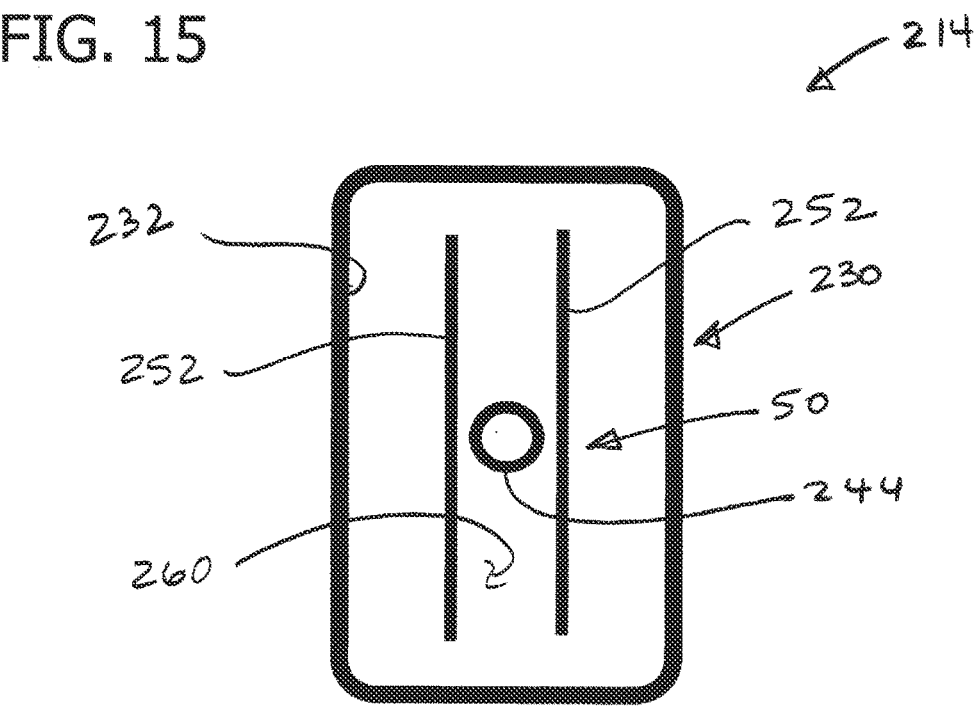
FIG. 15 is a schematic bottom plan view of the first container body portion of FIG. 9.
Figure 23:
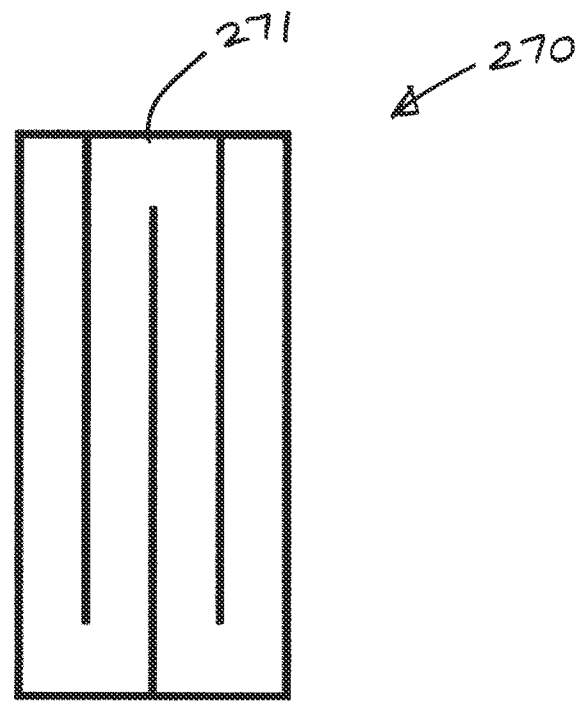
FIG. 23 is a front elevation of another embodiment of the absorbent insert.
Figure 24:
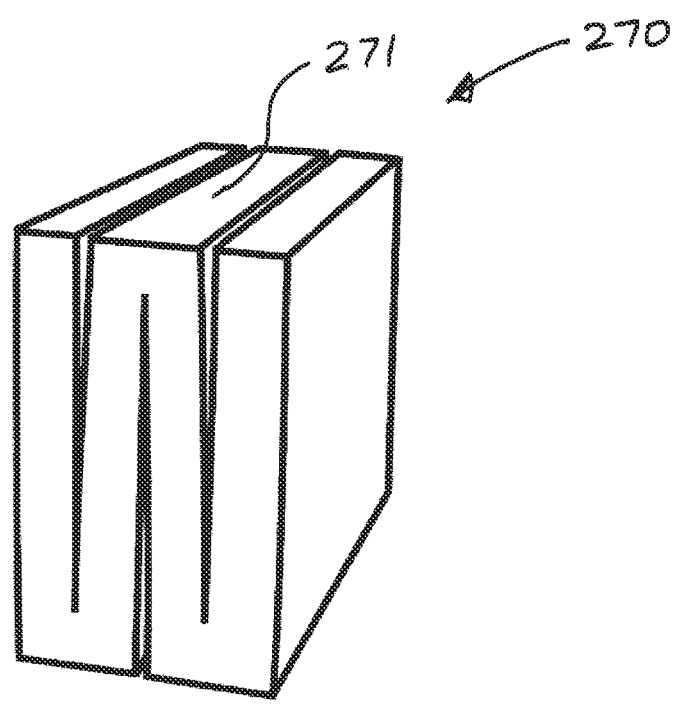
FIG. 24 is a perspective of the absorbent insert of FIG. 23.

The container may be of other configurations and designs without departing from the scope of the present invention. For example, another embodiment of the container is generally indicated at reference numeral 214 in FIGS. 9, 10, and 15. This embodiment is substantially similar to the container illustrated in FIGS. 7 and 8, with differences between disclosed hereinafter. Suitable teachings set forth above with respect to other embodiments of the container, including by not limited to the standoffs 90A, 90B, 90C, apply equally to the container 214. Unlike the baffle 50 of FIGS. 7 and 8, the baffle 250 of this container 214 includes two spaced apart baffle bodies 252 in opposing relationship to one another. The opposing baffle bodies 252 define the fluid passageway 260 therebetween, which is in fluid communication with the fluid inlet 244 and the fluid outlet 246. Referring to FIGS. 23 and 24, the absorbent insert 270 for use with this container 214 is folded into a W-shaped cross-sectional configuration. A folded middle portion 271 of the absorbent insert 270 is received in the fluid passageway 260 between the baffle bodies 252, such that liquid L (e.g., saliva) entering the fluid passageway may be absorbed by the absorbent insert. A free end of the folded middle portion 271 may be adjacent the fluid inlet 244 so that liquid L may be absorbed by the absorbent insert 270 generally open entering the container body 230. Like the absorbent insert 70 having the U-shaped cross-sectional configuration, the W-shaped configuration of the absorbent insert 270 envelopes the baffle 250. The flow of gas A (e.g., air) and/or liquid L through flow paths defined between the absorbent insert 270 and the baffle 250 and interior surface 232 of the container body 230 is shown in FIG. 10.

Figure 9:
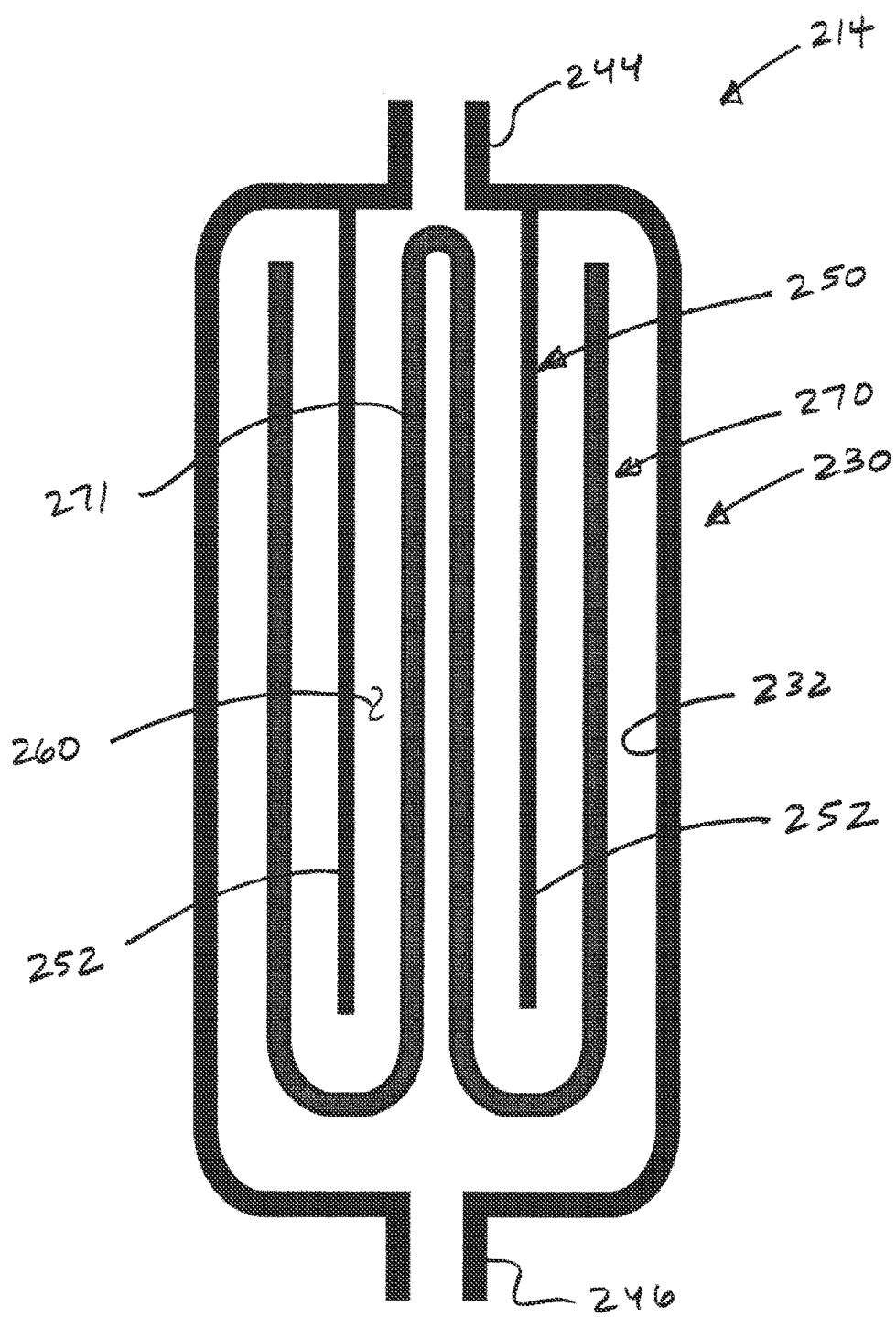
FIG. 9 is a schematic sectional view of another embodiment of the container.
Figure 10:
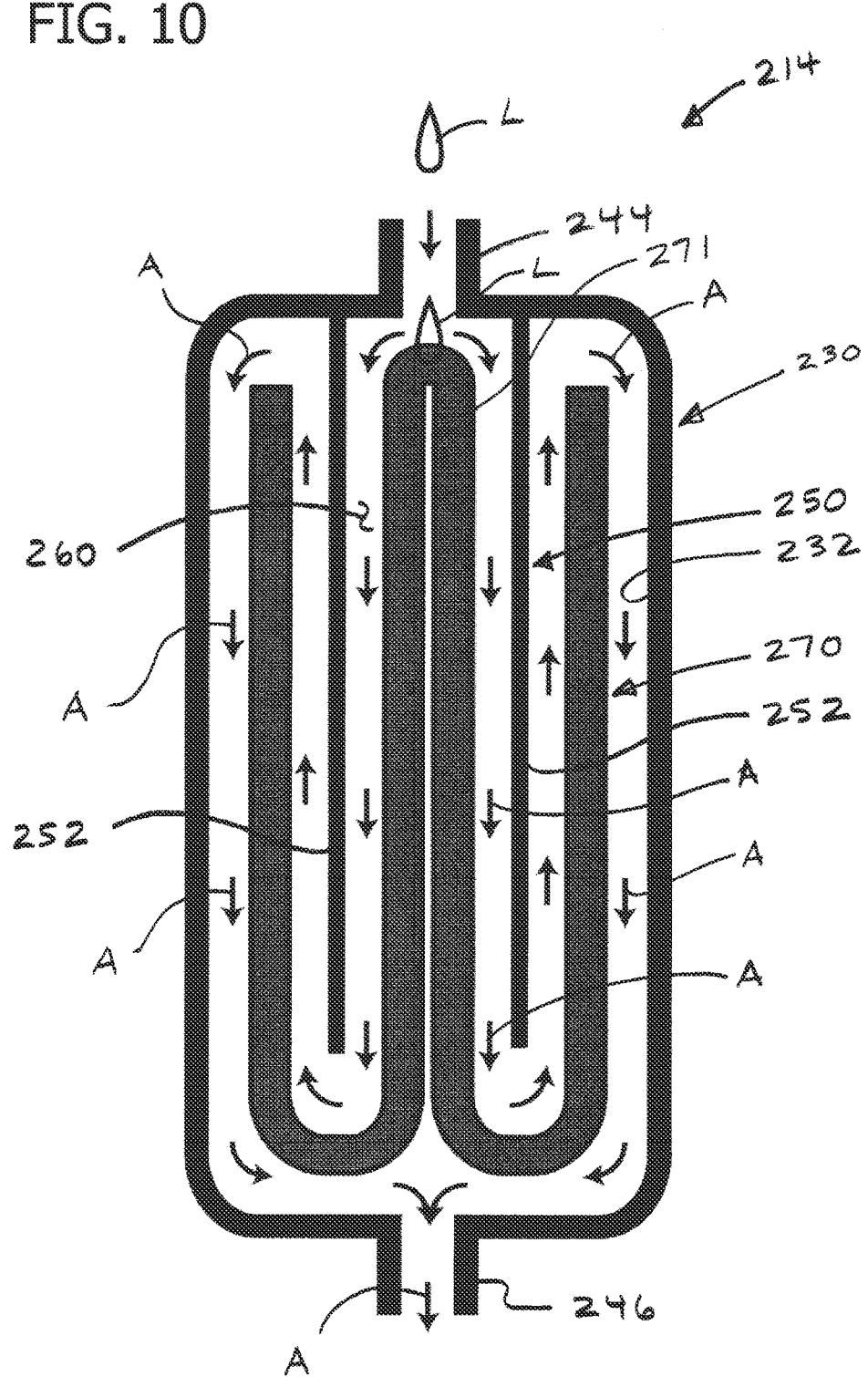
FIG. 10 is similar to FIG. 9, except showing liquid and gas entering the container, with liquid being absorbed by the absorbent insert and gas exiting the container.
Figure 12:
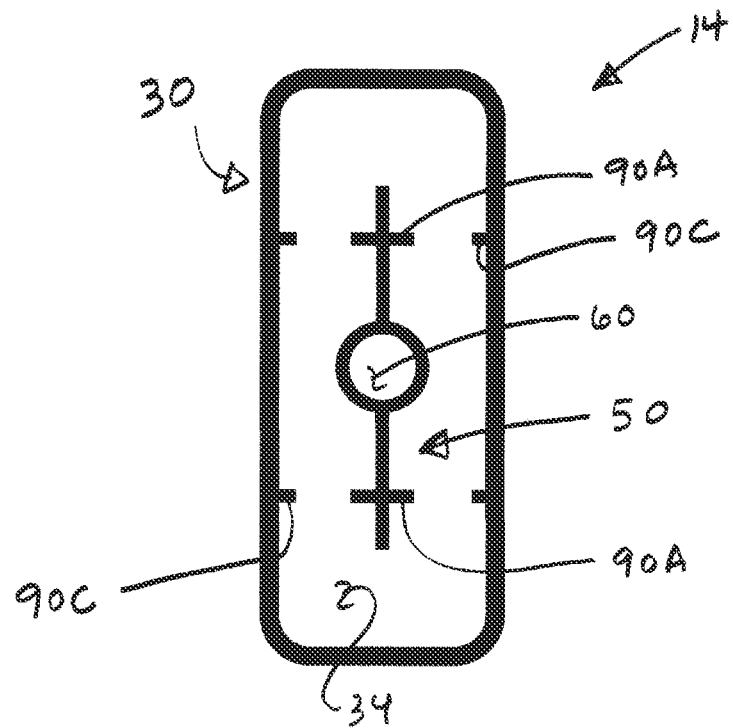
FIG. 12 is a schematic bottom plan view of a first container body portion of another embodiment of the container similar to the first container body portion of FIG. 11, except with fewer standoffs.
Figure 13:
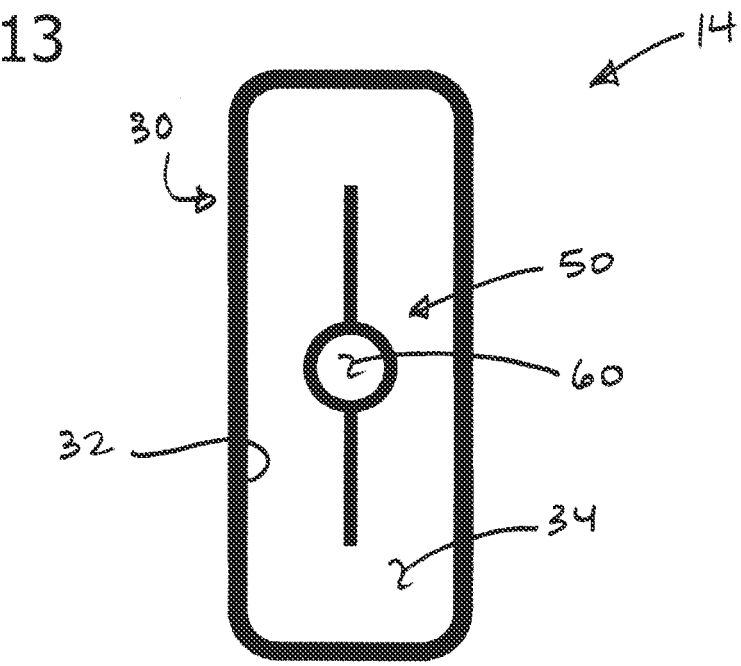
FIG. 13 is a schematic bottom plan view of a first container body portion of another embodiment of the container similar to the first container body portion of FIG. 12, except without any standoffs.
Figure 16:
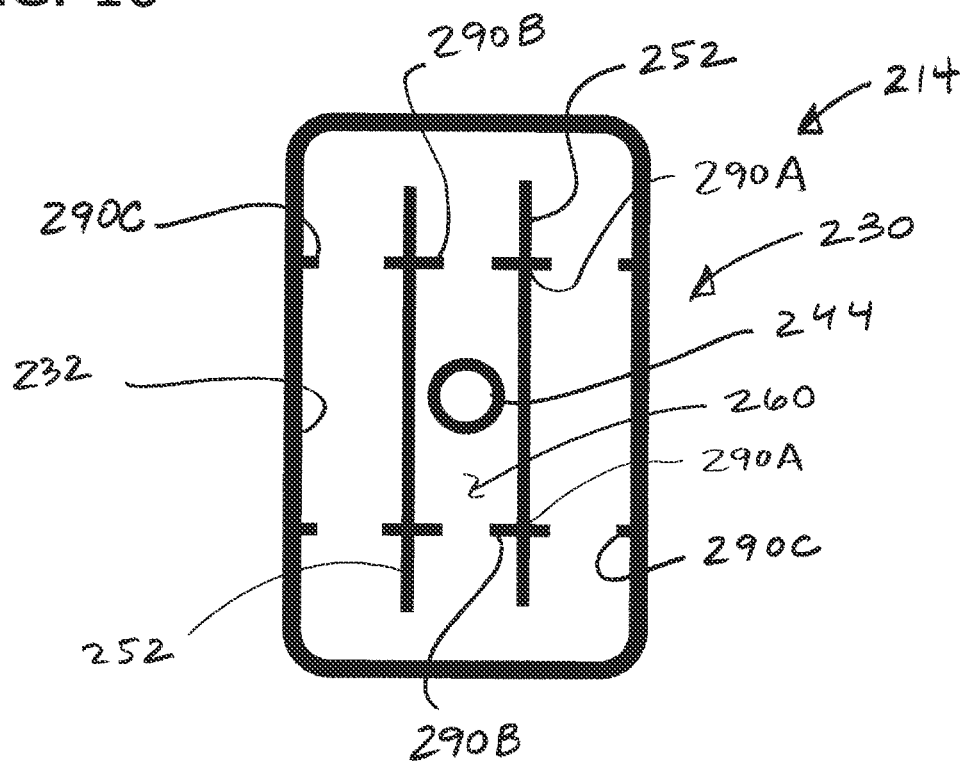
FIG. 16 is a schematic bottom plan view of a first container body portion of another embodiment of the container similar to the first container body portion of FIG. 15, except the interior baffle and the interior surface of the container include standoffs.
Figure 17:
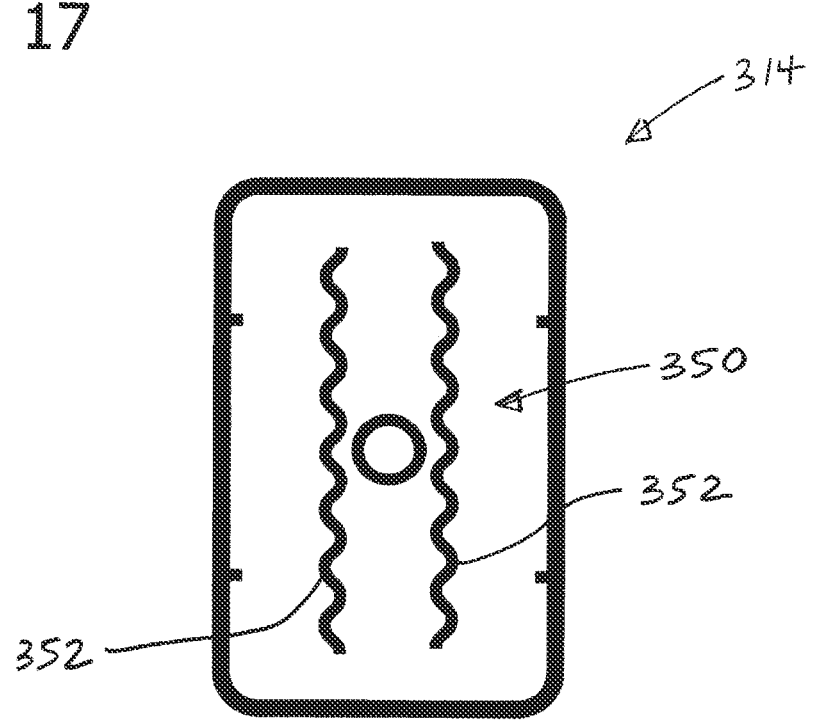
FIG. 17 is a schematic bottom plan view of a first container body portion of another embodiment of the container similar to the first container body portion of FIG. 16, except the interior baffle is free from standoffs and has a sinuous cross section.

Other variations of the container embodiment of FIGS. 9 and 10 are shown in FIGS. 16 and 17. FIG. 16 is a schematic showing the container 214 including standoffs 290A, 290B, 290C on at least one of the baffle bodies 252 and the interior surface 232 of the container body 230. The teachings of the standoffs 90A, 90B, 90C relating to FIGS. 3, 11, and 12 (for example) apply to this embodiment. FIG. 17 is a schematic showing the container 314 including a baffle 350 having the baffle bodies 352 having sinuous cross-sectional shapes. The teachings of the baffle 150 relating to FIG. 14 apply to this embodiment. Other variations of the container are possible.

Having described the invention in detail, it will be apparent that modifications and variations are possible without departing from the scope of the invention defined in the appended claims.

What is claimed is:

1. A container for collecting liquid drawn through a vacuum conduit from an oral cavity of a user by a vacuum pump of an oral negative-pressure therapy system, the container comprising:
    a container body having an interior surface defining an interior space;
    a fluid inlet for fluidly connecting the vacuum conduit to the interior space;
    a fluid outlet for fluidly connecting the vacuum pump to the interior space;
    an interior baffle connected to the container body and disposed in the interior space, the interior baffle configured to support an absorbent insert received thereon; and
    a fluid passageway extending from the fluid inlet along the interior baffle, wherein the fluid passageway fluidly connects the fluid inlet to the interior space when the absorbent insert is received on the interior baffle;
    wherein the interior baffle includes a baffle body and a plurality of baffle standoffs extending outward from the baffle body, wherein the baffle standoffs are configured to space the absorbent insert apart from the baffle body to define fluid flow paths between baffle body and the absorbent insert that are in fluid communication with the fluid passageway and the outlet.

2. The container set forth in claim 1, wherein at least some of the baffle standoffs of the interior baffle extend along the baffle body and are spaced apart from one another to define a plurality of flow channels extending along the baffle body.

3. The container set forth in claim 1, wherein the baffle body has a connected end connected to the container body and a free end spaced apart from and generally opposing a portion of the interior surface of the container body, wherein at least some of the baffle standoffs of the interior baffle extend axially outward from the free end of the baffle body to define a plurality of flow channels at the free end of the baffle body.

4. The container set forth in claim 1, wherein the container body includes a plurality of body standoffs extending outward from the interior surface of the container body, wherein the body standoffs are configured to space the absorbent insert apart from the interior surface of the container body to define fluid flow paths between the interior surface of the container body and the absorbent insert that are in fluid communication with the fluid passageway and the outlet.

5. The container set forth in claim 1, wherein fluid passageway extends through the interior baffle.

6. The container set forth in claim 5, wherein the baffle has a connected end connected to the container body and a free end spaced apart from and generally opposing a portion of the interior surface of the container body, wherein the fluid passageway extends through the free end of the baffle.

7. The container set forth in claim 1, wherein the baffle has a connected end connected to the container body and a free end spaced apart from and generally opposing a portion of the interior surface of the container body to define a clearance space in which a portion of the absorbent insert is received when the absorbent insert is received on the interior baffle.

8. The container set forth in claim 7, wherein container body has opposite first and second ends and a sidewall extending between the first and second ends, wherein the interior surface of the sidewall is spaced apart from and surrounds the baffle to define an annular space in which a portion of the absorbent insert is received when the absorbent insert is received on the interior baffle.

9. The container set forth in claim 8, wherein the clearance space and the annular space define a cavity having a U-shaped cross section in which the absorbent insert is received when the absorbent insert is received on the interior baffle.

10. The container set forth in claim 1, wherein the interior baffle has an exterior surface defining a plurality of flow channels extending along the interior baffle to define fluid flow paths between the interior baffle and the absorbent insert that are in fluid communication with the fluid passageway and the outlet.

11. The container set forth in claim 10, wherein the interior baffle has a sinuous cross-sectional shape defining the plurality of flow channels.

12. The container set forth in claim 10, wherein the interior baffle includes a baffle body and a plurality of baffle standoffs extending outward from the baffle body to define the plurality of flow channels.

13. The container set forth in claim 1, wherein the interior baffle comprises first and second baffle bodies spaced apart from one another, wherein the fluid passageway is disposed between the first and second baffle bodies.

14. The container set forth in claim 1, wherein the container body includes a first body portion and a second body portion removably attachable to the first body portion for opening and closing the container body.

15. The container set forth in claim 14, wherein the inlet and the baffle associated with the first body portion, wherein the outlet is associated with the second body portion.

16. An absorbent insert for a container of an oral negative-pressure therapy system, the container defining an interior space and including an interior baffle connected to the container body and disposed in the interior space, the absorbent insert comprising:
an absorbent pouch having an open end, an opposite closed end, an exterior surface, and an interior surface defining an interior cavity sized and shaped to receive the baffle therein such that the absorbent pouch substantially envelopes the interior baffle when the baffle is inserted into the absorbent pouch through the open end.

17. The absorbent insert set forth in claim 16, wherein the absorbent pouch includes a liquid-permeable inner layer defining the interior surface of the absorbent pouch, an outer layer defining the exterior surface of the absorbent pouch, and an absorbent core enveloped between the inner and outer layers, wherein the absorbent core comprises an absorbent material configured to absorb liquid introduced into the container.

18. The absorbent insert set forth in claim 16, wherein the interior surface of the absorbent pouch includes a plurality of formations configured to burst bubbles formed in liquid introduced into the container when the bubbles contact the interior surface of the absorbent pouch.

19. A method of manufacturing the absorbent insert set forth in claim 16, comprising the steps of:
providing a liquid permeable inner layer joined to an outer layer to form a two ply construction;
folding the two ply construction in substantially half at a midline thereof; and
sealing lateral sides of the folded two ply construction to form the absorbent pouch, wherein the liquid permeable inner layer defines the interior surface of the pouch.

20. The method of manufacturing the absorbent insert set forth in claim 19, further comprising providing an absorbent core enveloped between the inner and outer layers.

21. The method of manufacturing the absorbent insert set forth in claim 19, further comprising sealing a side of the folded two ply construction opposite the midline.

22. An oral negative-pressure therapy system comprising:
an oral appliance including an inlet for fluid communication with an oral cavity of a user;
a conduit in fluid communication with the inlet of the oral appliance;
a negative-pressure pump in fluid communication with the conduit for creating a negative pressure in the oral cavity of the user;
a container in fluid communication with the conduit and the negative-pressure pump for collecting liquid drawn through the conduit from the oral cavity of the user by the negative-pressure pump, the container including
a container body having an interior surface defining an interior space,
a fluid inlet for fluidly connecting the conduit to the interior space,
a fluid outlet for fluidly connecting the negative-pressure pump to the interior space,
an interior baffle connected to the container body and disposed in the interior space, the interior baffle configured to support a absorbent insert received thereon, and
a fluid passageway extending from the fluid inlet along the interior baffle, wherein the fluid passageway fluidly connects the fluid inlet to the interior space when the absorbent insert is received on the interior baffle; and an absorbent pouch having an exterior surface, and an interior surface defining an interior cavity sized and shaped to receive the baffle therein such that the absorbent pouch substantially envelopes the interior baffle;

wherein a fluid path in the interior space fluidly connects the fluid passageway to the fluid outlet, at least a portion of the fluid path being defined between the interior baffle and the absorbent pouch.

\* \* \* \* \*